US012193643B2

United States Patent
McDowall et al.

(10) Patent No.: US 12,193,643 B2
(45) Date of Patent: *Jan. 14, 2025

(54) DYNAMIC APERTURE POSITIONING FOR STEREO ENDOSCOPIC CAMERAS

(71) Applicant: INTUITIVE SURGICAL OPERATIONS, INC., Sunnyvale, CA (US)

(72) Inventors: Ian E. McDowall, San Francisco, CA (US); Arthur Louis Berman, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/478,586

(22) Filed: Sep. 29, 2023

(65) Prior Publication Data

US 2024/0099565 A1    Mar. 28, 2024

Related U.S. Application Data

(63) Continuation of application No. 16/998,056, filed on Aug. 20, 2020, now Pat. No. 11,805,984, which is a
(Continued)

(51) Int. Cl.
*A61B 1/00*    (2006.01)
*G02B 23/24*   (2006.01)
(Continued)

(52) U.S. Cl.
CPC ...... *A61B 1/00193* (2013.01); *A61B 1/00009* (2013.01); *G02B 23/2415* (2013.01);
(Continued)

(58) Field of Classification Search
None
See application file for complete search history.

(56) References Cited

U.S. PATENT DOCUMENTS

| 4,924,853 A | 5/1990 | Jones, Jr. et al. |
| 5,588,948 A | 12/1996 | Takahashi et al. |

(Continued)

FOREIGN PATENT DOCUMENTS

| CN | 103210348 A | 7/2013 |
| CN | 104274146 A | 1/2015 |

(Continued)

OTHER PUBLICATIONS

Extended European Search Report for Application No. EP19782397. 4, mailed on Nov. 22, 2021, 8 pages.

(Continued)

*Primary Examiner* — John P Leubecker
(74) *Attorney, Agent, or Firm* — Haynes & Boone, LLP.

(57) ABSTRACT

A stereoscopic endoscope comprises at least one image sensor for sensing a first image and a second image of a pair of stereo images. The first image is sensed based on light passing through a first aperture within the stereoscopic endoscope. The second image is sensed based on light passing through a second aperture within the stereoscopic endoscope. The stereoscopic endoscope further comprises a liquid crystal layer disposed between two layers of glass. The two layers of glass comprise a first arrangement of electrodes, such that each of the first aperture and the second aperture is created in the liquid crystal layer using a portion of the first arrangement of electrodes. A polarization state associated with each of the first and second apertures are controlled using corresponding control signals provided through the first arrangement of electrodes.

20 Claims, 17 Drawing Sheets

Related U.S. Application Data continuation of application No. 16/443,774, filed on Jun. 17, 2019, now Pat. No. 10,754,241, which is a continuation of application No. 15/956,655, filed on Apr. 18, 2018, now Pat. No. 10,365,554.

(60) Provisional application No. 62/652,826, filed on Apr. 4, 2018.

(51) Int. Cl.
| | |
|---|---|
| *G03B 17/02* | (2021.01) |
| *G03B 35/10* | (2021.01) |
| *G03B 35/18* | (2021.01) |
| *G02B 30/34* | (2020.01) |
| *H04N 13/225* | (2018.01) |

(52) U.S. Cl.
CPC ............ *G03B 17/02* (2013.01); *G03B 35/10* (2013.01); *G03B 35/18* (2013.01); *G02B 30/34* (2020.01); *H04N 13/225* (2018.05)

(56) References Cited

U.S. PATENT DOCUMENTS

| | | | |
|---|---|---|---|
| 5,689,365 | A | 11/1997 | Takahashi et al. |
| 5,876,325 | A | 3/1999 | Mizuno et al. |
| 5,914,810 | A | 6/1999 | Watts |
| 6,154,315 | A | 11/2000 | Street |
| 7,180,660 | B2 | 2/2007 | Hauger et al. |
| 7,280,283 | B1 | 10/2007 | Kasai |
| 7,768,702 | B2 | 8/2010 | Hirose et al. |
| 8,081,380 | B2 | 12/2011 | Mckinley |
| 8,639,109 | B2 | 1/2014 | Aoki et al. |
| 8,749,620 | B1 | 6/2014 | Knight et al. |
| 10,330,914 | B2 | 6/2019 | Togino |
| 10,365,554 | B1 | 7/2019 | McDowall et al. |
| 10,754,241 | B2 | 8/2020 | McDowall et al. |
| 11,805,984 | B2 | 11/2023 | McDowall et al. |
| 2001/0012053 | A1 | 8/2001 | Nakamura et al. |
| 2002/0008907 | A1 | 1/2002 | Yamamoto |
| 2002/0141057 | A1 | 10/2002 | Weissman et al. |
| 2002/0154215 | A1 | 10/2002 | Schechterman et al. |
| 2005/0140820 | A1 | 6/2005 | Takeuchi et al. |
| 2005/0159641 | A1 | 7/2005 | Kanai |
| 2005/0237606 | A1 | 10/2005 | Greenberg et al. |
| 2008/0212838 | A1 | 9/2008 | Frigerio et al. |
| 2010/0007718 | A1 | 1/2010 | Rohaly, Jr. et al. |
| 2010/0019170 | A1 | 1/2010 | Hart et al. |
| 2011/0115882 | A1 | 5/2011 | Shahinian et al. |
| 2012/0008195 | A1 | 1/2012 | Hoegele et al. |
| 2012/0140037 | A1 | 6/2012 | Galstian et al. |
| 2012/0188347 | A1 | 7/2012 | Mitchell |
| 2012/0206571 | A1 | 8/2012 | Kanamori et al. |
| 2012/0300033 | A1 | 11/2012 | Singh et al. |
| 2013/0063569 | A1 | 3/2013 | Sato et al. |
| 2013/0102846 | A1 | 4/2013 | Sjostrom et al. |
| 2013/0176566 | A1 | 7/2013 | Mitchell et al. |
| 2015/0073219 | A1 | 3/2015 | Nagae et al. |
| 2016/0171679 | A1 | 6/2016 | Ishiwata et al. |
| 2016/0178886 | A1 | 6/2016 | Shechterman et al. |
| 2017/0245744 | A1 | 8/2017 | McDowall |
| 2017/0280970 | A1 | 10/2017 | Sartor et al. |
| 2019/0285869 | A1 | 9/2019 | Zhao et al. |
| 2020/0379334 | A1 | 12/2020 | McDowall et al. |

FOREIGN PATENT DOCUMENTS

| | | |
|---|---|---|
| CN | 104887314 A | 9/2015 |
| DE | 102010027079 A1 | 1/2012 |
| DE | 102013215422 A1 | 2/2015 |
| DE | 102014206513 A1 | 10/2015 |
| DE | 102015217079 A1 | 3/2017 |
| RU | 2413205 C1 | 2/2011 |

OTHER PUBLICATIONS

International Preliminary Report on Patentability and Written Opinion for Application No. PCT/US2019/024608, mailed on Oct. 15, 2020, 8 pages.

International Search Report and Written Opinion for Application No. PCT/US2019/024608, mailed on Jul. 11, 2019, 13 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

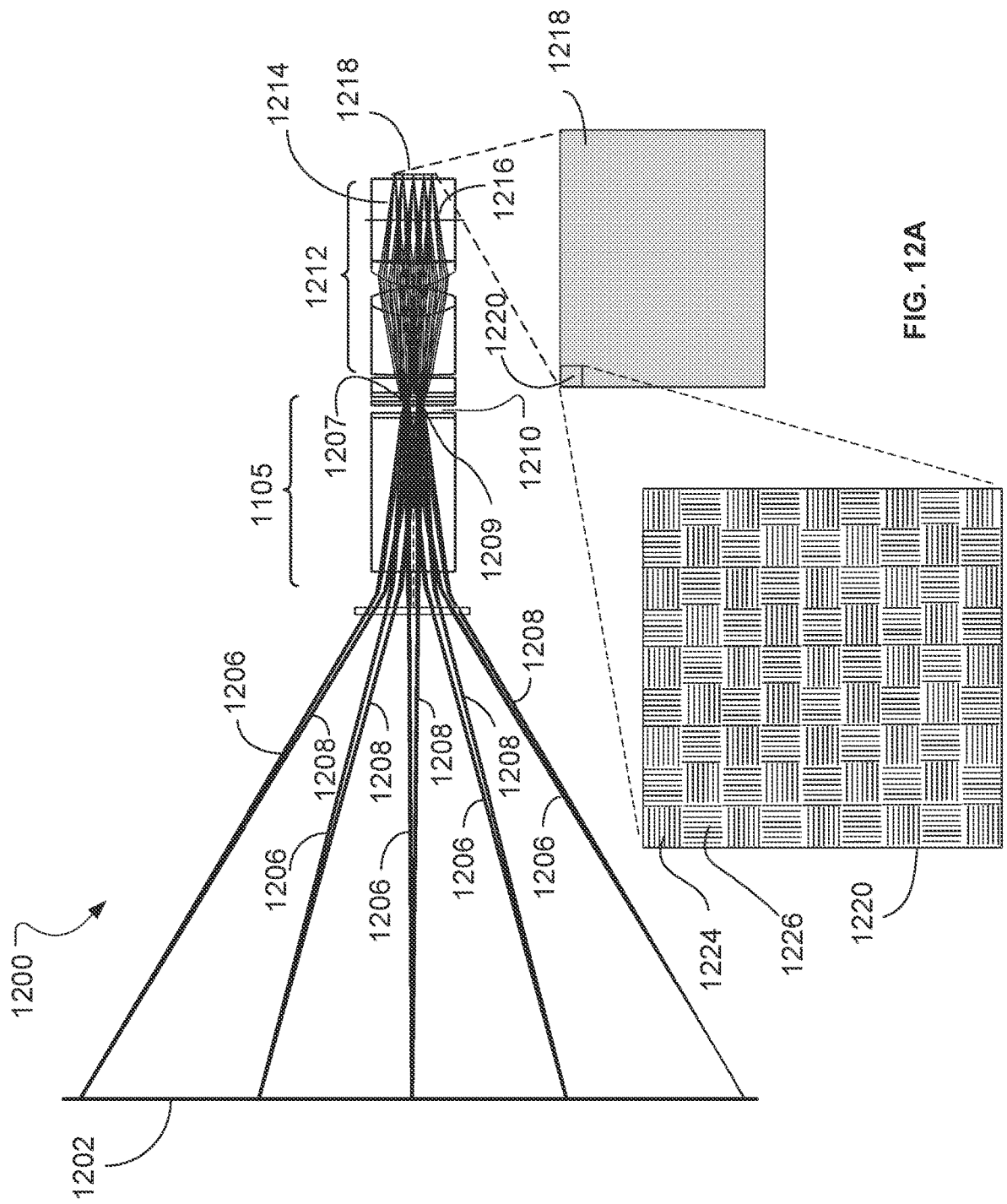

DYNAMIC APERTURE POSITIONING FOR STEREO ENDOSCOPIC CAMERAS

PRIORITY CLAIM

This application is a continuation of U.S. application Ser. No. 16/998,056 (now U.S. Pat. No. 11,805,984), filed on Aug. 20, 2020, which is a continuation of U.S. application Ser. No. 16/443,774 now U.S. Pat. No. 10,754,241), filed on Jun. 17, 2019, which is a continuation of U.S. application Ser. No. 15/956,655 (now U.S. Pat. No. 10,365,554), filed on Apr. 18, 2018, which claims priority to U.S. Provisional Application 62/652,826, filed on Apr. 4, 2018. The entire contents of which each of the foregoing applications are incorporated herein by reference.

TECHNICAL FIELD

This disclosure relates to three-dimensional (3D) endoscopes that may be used in surgical systems.

BACKGROUND

Minimally invasive surgical systems are being developed to reduce the trauma experienced by patients undergoing surgical interventions. These systems require only small incisions and surgeons use stick like cameras and instruments to perform the procedure. In addition to reducing trauma, teleoperated systems of this type increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site through a display device. Based on visual feedback received through the display device, the surgeon performs the surgical procedures on the patient by manipulating master control input devices, which in turn control the motion of tele-robotic instruments.

SUMMARY

The technology described herein describes stereoscopic cameras with controllable pupil locations. The controllable pupil locations allow a stereoscopic view that adapts to the axial rotation of an endoscope with an angled view. Methods are described as to how to control the location of the pupils to create a natural stereo view during scope rotation or during head motion by a viewer. The device is electronic and may be controlled through software.

In one aspect, this document features a method for generating a view of a scene, the method including determining, by one or more processing devices, an angle of orientation defined by a line connecting a first aperture location and a second aperture location of a stereoscopic endoscope with respect to a reference orientation. The method also includes adjusting at least one of the first and second aperture locations, while maintaining a spacing between the first and second aperture locations, to maintain the angle of orientation across multiple endoscope orientations. The method also includes creating an aperture at each of the first and second aperture locations, and generating a representation of the view for presentation on a display device associated with the stereoscopic endoscope using signals (representing image data) based on light captured through the apertures created at the first and second aperture locations.

In another aspect, this document describes a system that includes a stereoscopic endoscope, a display device, and one or more processing devices. The stereoscopic endoscope includes at least one image sensor for sensing a first image and a second image of a pair of stereo images. The first and second images are sensed based on light passing through apertures electronically defined at a first aperture location and a second aperture location, respectively, on a liquid crystal layer within the endoscope. The one or more processing devices are configured to determine an angle of orientation defined by a line connecting the first aperture location and the second aperture location of the stereoscopic endoscope with respect to a reference orientation, adjust at least one of the first and second aperture locations, while maintaining a spacing between the first and second aperture locations, to maintain the angle of orientation across multiple endoscope orientations, and create an aperture at each of the first and second aperture locations. The one or more processing devices are also configured to generate a representation of views of a surgical scene using the pair of stereo images captured through the apertures created at the first and second aperture locations. The display device is configured to presenting the representation of the views.

In another aspect, this document describes one or more machine-readable storage devices having encoded thereon computer readable instructions for causing one or more processing devices to perform various operations. The operations include determining an angle of orientation defined by a line connecting a first aperture location and a second aperture location of a stereoscopic endoscope with respect to a reference orientation, and adjusting at least one of the first and second aperture locations, while maintaining a spacing between the first and second aperture locations, to maintain the angle of orientation across multiple endoscope orientations. The operations also include creating an aperture at each of the first and second aperture locations, and generating a representation of a view for presentation on a display device associated with the stereoscopic endoscope using signals based on light captured through the apertures created at the first and second aperture locations.

Implementations of the above aspects can include one or more of the following features. The reference orientation can be perpendicular to the direction of earth's gravity. Information indicative of an orientation of the head of a user operating the stereoscopic endoscope can be received, and the reference orientation can be determined in accordance with the information indicative of the orientation of the head of the user. Adjusting at least one of the first and second aperture locations can include selecting locations of a pair of liquid crystal display (LCD) segments from a set of LCD segments disposed in a substantially annular configuration in an optical path of the stereoscopic endoscope. Creating the apertures at each of the first and second aperture locations can include controlling a first LCD segment in the pair of LCD segments such that the first LCD segment changes to a state in which the first LCD segment allows more light to pass through as compared to a different, relatively dark state, and controlling a second LCD segment in the pair of LCD segments such that the second LCD segment changes to a state in which the second LCD segment allows more light to pass through as compared to a different, relatively dark state. The first and second LCD segments can be controlled to acquire a first image and a second image, respectively, substantially concurrently. Light passing through the first LCD segment can pass through a first polarizer, and light passing through the second LCD segment can pass through a second polarizer that polarizes light differently from the first polarizer. The first polarizer can be orthogonal with respect to the second polarizer. The light passing through the apertures created at the first and second aperture locations can be sensed using a first sensor and a second sensor, respectively, the first and second sensors being disposed on two opposing sides of a polarizing beam splitter. The apertures can be created at the first and second aperture locations in a sequential pattern. The light passing through the apertures created at the first and second aperture locations can be sensed using a single sensor. The representation of the view may be presented on the display device. Responsive to presenting the representation of the view on the display device, user input pertaining to operating a surgical device at a surgical scene may be received.

In another aspect, this document features a stereoscopic endoscope that includes at least one image sensor for sensing a first image and a second image of a pair of stereo images. The first image is sensed based on light passing through a first aperture within the endoscope, and the second image is sensed based on light passing through a second aperture within the endoscope. A liquid crystal layer disposed between two layers of glass includes a first arrangement of electrodes, such that each of the first aperture and the second aperture is created in the liquid crystal layer using a portion of the first arrangement of electrodes.

Implementations can include one or more of the following features. The light passing through the first aperture can be polarized differently as compared to the light passing through the second aperture. The stereoscopic endoscope can include a first image sensor, a second image sensor, and an optical element that directs incident light to the first image sensor or the second image sensor based on polarization state of the incident light. Each of the first aperture and the second aperture can be controlled to be located at various locations on the liquid crystal layer in response to corresponding control signals provided through the first arrangement of electrodes. Locations of the first and second apertures can be controllable in accordance with an orientation of the endoscope with respect to a reference orientation. The stereoscopic endoscope can include a first image sensor and a second image sensor, wherein the first image and the second image are sensed by the first image sensor and the second image sensor, respectively, substantially concurrently. The first image and the second image can be sensed by a single image sensor sequentially. The stereoscopic endoscope can include a first portion housing a front end lens assembly, and a second portion including an elongated shaft that houses the liquid crystal layer and the at least one image sensor. The second portion can be disposed at an angle with respect to the first portion. The angle can be one of: 0°, 30°, and 45°. A location of at least one of the first and second apertures can be electronically adjusted using the first arrangement of electrodes to maintain an angle between (i) a line connecting the first and second apertures, and (ii) a reference orientation. The angle between (i) the line connecting the first and second apertures, and (ii) the reference orientation can be maintained while also maintaining a spacing between the first and second apertures. The angle between (i) a line connecting the first and second apertures, and (ii) the reference orientation can be maintained using one or more control signal calculated based on one or more previously captured images.

In another aspect, this document features a system that includes a stereoscopic endoscope, a display device, and one or more processing devices. The stereoscopic endoscope includes at least one image sensor for sensing a first image and a second image of a pair of stereo images. The first and second images are sensed based on light passing through apertures electronically defined at a first aperture location and a second aperture location, respectively, on a liquid crystal layer within the endoscope. The one or more processing devices are configured to determine an angle of orientation defined by a line connecting the first aperture location and the second aperture location of the stereoscopic endoscope with respect to a reference orientation, and adjust at least one of the first and second aperture locations, while maintaining a spacing between the first and second aperture locations, to maintain the angle of orientation across multiple endoscope orientations. The one or more processing devices are also configured to create an aperture at each of the first and second aperture locations, and generate representation of views using the pair of stereo images captured through the apertures created at the first and second aperture locations. The display device is configured for presenting the representation of the views.

In another aspect, this document features one or more machine-readable storage devices having encoded thereon computer readable instructions for causing one or more processing devices to perform various operations. The operations include determining an angle of orientation defined by an orientation of a line connecting a first aperture location and a second aperture location of a stereoscopic endoscope relative to a reference orientation, and adjusting at least one of the first and second aperture locations, while maintaining a spacing between the first and second aperture locations, to maintain the angle of orientation, in response to movement of the stereoscopic endoscope. The operations further include capturing image data through apertures created at the first and second aperture locations.

In another aspect, this document features a method for generating a two views of a scene, the method comprising, generating two or more regions of a first liquid crystal layer for allowing polarized light to pass through such regions, and allowing said light to pass through a polarizer. The method also includes allowing said light to pass through a second liquid crystal layer, and separating said light, on the basis of polarization, into substantially two portions, each portion including light of predominantly one polarization state.

In another aspect, this document describes a stereo endoscope that includes a two pupil optical system wherein each pupil is orthogonally polarized, and wherein light from the polarized pupils are split onto two image sensors based on polarization.

In another aspect, this document features a stereo endoscope that includes a two pupil optical system wherein each pupil is orthogonally polarized, and wherein light from the polarized pupils casting onto a single image sensor with a checkerboard of pixels sensitive to orthogonal polarization states.

Some or all of the embodiments described herein may provide one or more of the following advantages. By providing a split-pupil endoscope camera in which the pupil locations are controlled using liquid crystal display elements, an electronically controllable imaging apparatus with few, if any, mechanically moving parts may be implemented within the space-constrained and/or resource constrained environment of an endoscope. The pupil locations may be controlled based on information associated with the orientation of a surgeon's head. Other control inputs may be used as well and may facilitate certain image processing requirements. This in turn can keep the two pupils separated by a predetermined distance along a reference direction even when the camera is rotated during the operation of an endoscope. The direction of separation of the pupils relative to gravity for example may be controlled at will. Maintaining such predetermined distance between the stereoscopic pupils may allow for displaying accurate 3D representations for different orientations of the endoscope. In some cases, such representations may be consistent with the natural way a surgeon would view the corresponding surgical scene, and therefore may contribute to improving the user-experience for the surgeon. The separation distance of the pupils (or inter pupillary distance) may also be controlled if desired.

BRIEF DESCRIPTION OF THE DRAWINGS

FIG. 12A is a schematic diagram illustrating optical paths through an example of a 0° stereoscopic endoscope that uses one sensor for sensing both stereoscopic images substantially simultaneously.

DETAILED DESCRIPTION

Figure 2:
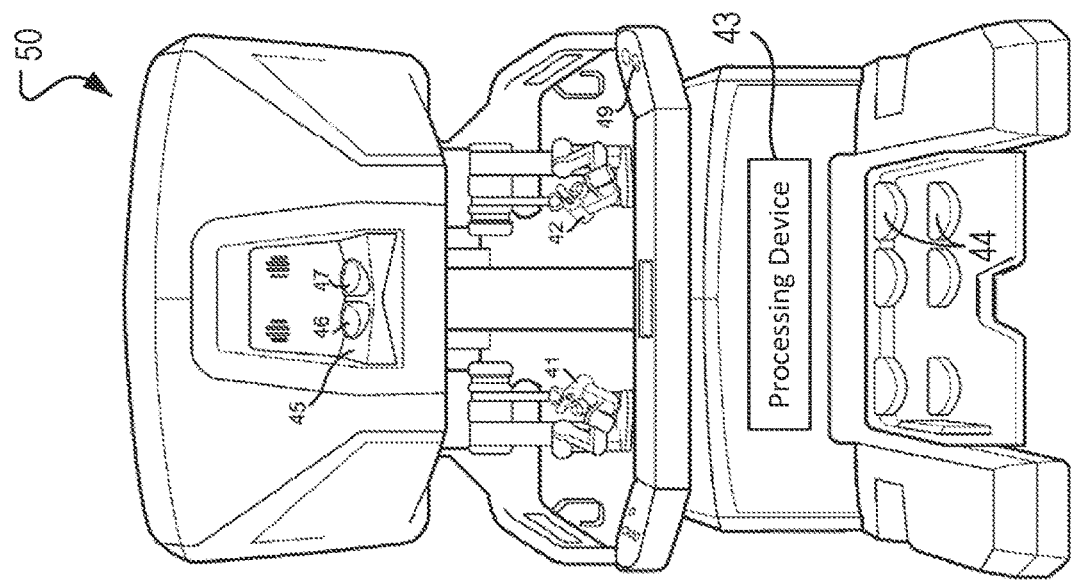
FIG. 2 is a front view of an example surgeon console of a computer-assisted tele-operated surgery system.

This document describes technology that facilitates automatic correction of camera aperture positions in stereoscopic endoscopes such that the aperture positions remain substantially fixed with respect to a reference frame even when the endoscope is oriented at different angles during a surgery. In some implementations, this can allow a more natural perception of the 3D representation of the surgical scene as presented via stereo images on a surgeon's console. For example, the surgeon may visualize the surgical scene more naturally (e.g., without having to tilt or reorient her head) even when the endoscope is oriented at arbitrary angles. In some cases, this can improve the overall user-experience for the surgeon during surgical procedures. By allowing for aperture positions to be controlled electronically, potentially with few or no moving mechanical parts, the technology described herein facilitates implementations suited to space constrained and/or resource constrained environments of stereoscopic endoscopes. Endoscope in this context may be a rigid device that incorporates optics and one or more image sensors to create a camera system; a flexible device that has a wristed section; a flexible device with a camera at the distal end; an optical endoscope (sometimes referred to as a Hopkins endoscope) with a camera, or a similar device.

Aspects of the technology are described primarily in terms of an implementation using da Vinci® surgical systems developed by Intuitive Surgical, Inc. of Sunnyvale, California. Examples of such surgical systems are the da Vinci® Xi™ Surgical System (Model IS4000). It should be understood that aspects disclosed herein may be embodied and implemented in various ways, including computer-assisted, non-computer-assisted, and hybrid combinations of manual and computer-assisted embodiments and implementations. Implementations on da Vinci® Surgical Systems, e.g. the Model IS4000 are described for illustrative purposes, and are not to be considered as limiting the scope of the inventive aspects disclosed herein. As applicable, inventive aspects may be embodied and implemented in both relatively smaller, hand-held, hand-operated devices and relatively larger systems that have additional mechanical support, as well as in other embodiments of computer-assisted tele-operated medical devices. While the technology is described primarily with reference to an example of a peer-in display, the technology may also be used in other types of wearable or non-wearable display devices such as a head-mounted display device used, for example, in virtual or augmented reality (VR/AR) systems. The images captured may also be displayed on a large format display such as a 3D TV device, projected onto a screen, or viewed by a user wearing stereo glasses. Alternatively, an auto-stereo type display may be used. Examples of an auto-stereo device include a lenticular liquid crystal display (LCD) that may also incorporate head and or eye tracking of the viewer (user).

Figure 1:
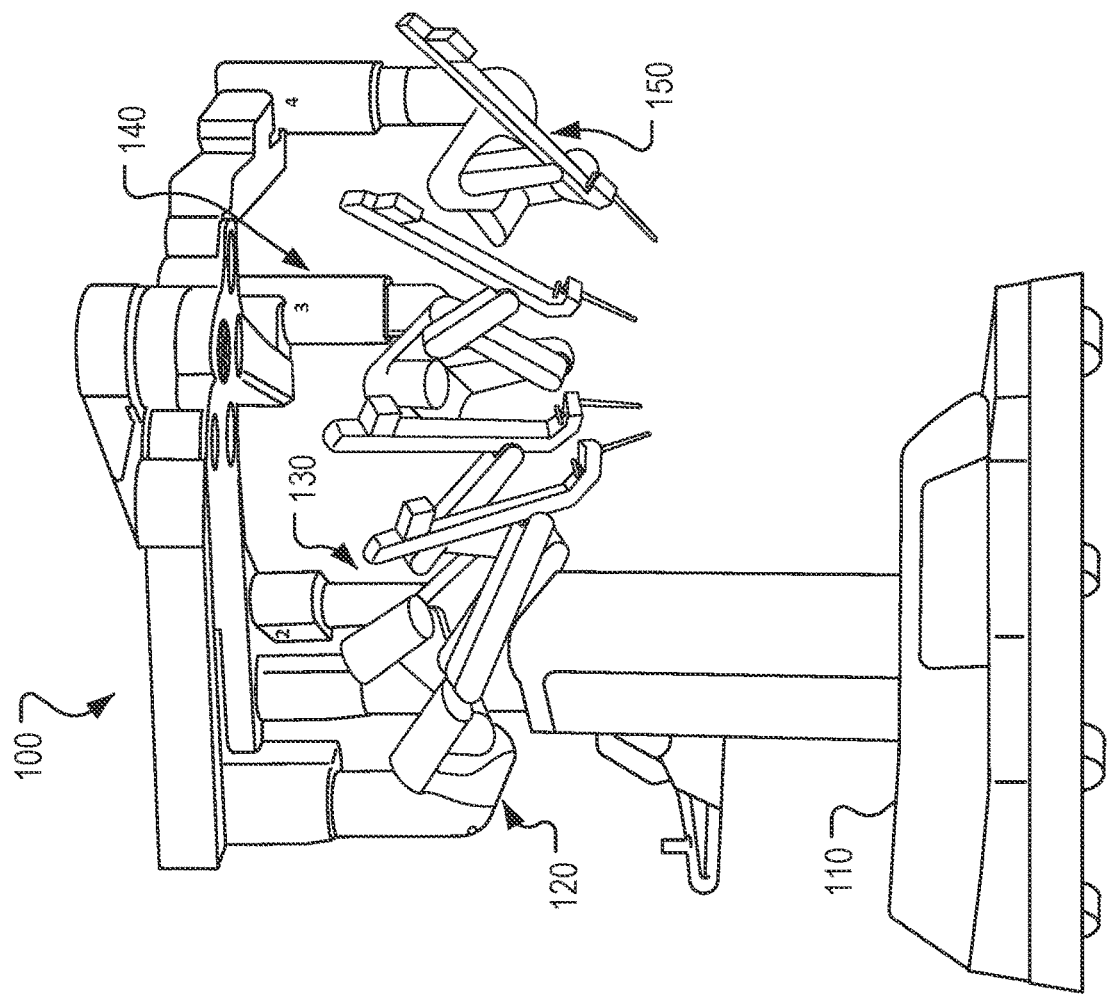
FIG. 1 is a perspective view of an example patient-side cart of a computer-assisted tele-operated surgery system.

Referring to FIGS. 1 and 2, systems for minimally invasive computer-assisted telesurgery (also referred to as MIS) can include a patient-side cart 100 and a surgeon console 50. Telesurgery is a general term for surgical systems where the surgeon uses some form of remote control, e.g., a servomechanism, or the like, to manipulate surgical instrument movements rather than directly holding and moving the instruments by hand. The robotically manipulatable surgical instruments can be inserted through small, minimally invasive surgical apertures to treat tissues at surgical sites within the patient body, avoiding the trauma associated with rather large incisions required for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

In the depicted embodiment, the patient-side cart 100 includes a base 110, a first robotic manipulator arm assembly 120, a second robotic manipulator arm assembly 130, a third robotic manipulator arm assembly 140, and a fourth robotic manipulator arm assembly 150. Each robotic manipulator arm assembly 120, 130, 140, and 150 is pivotably coupled to the base 110. In some embodiments, fewer than four or more than four robotic manipulator arm assemblies may be included as part of the patient-side cart 100. While in the depicted embodiment, the base 110 includes casters to allow ease of mobility, in some embodiments the patient-side cart 100 is fixedly mounted to a floor, ceiling, operating table, structural framework, or the like.

In a typical application, two of the robotic manipulator arm assemblies 120, 130, 140, or 150 hold surgical instruments and a third holds a stereo endoscope. The remaining robotic manipulator arm assembly is available so that a third instrument may be introduced at the work site. Alternatively, the remaining robotic manipulator arm assembly may be used for introducing a second endoscope or another image-capturing device, such as an ultrasound transducer, to the work site.

Each of the robotic manipulator arm assemblies 120, 130, 140, and 150 is conventionally formed of links that are coupled together and manipulated through actuatable joints. Each of the robotic manipulator arm assemblies 120, 130, 140, and 150 includes a setup arm and a device manipulator. The setup arm positions its held device so that a pivot point occurs at its entry aperture into the patient. The device manipulator may then manipulate its held device so that it may be pivoted about the pivot point, inserted into and retracted out of the entry aperture, and rotated about its shaft axis.

In the depicted embodiment, the surgeon console 50 includes a stereoscopic peer-in display 45 so that the user may view the surgical work site in stereo vision from images captured by the stereoscopic camera used in conjunction with the patient-side cart 100. Left and right eyepieces, 46 and 47, are provided in the stereoscopic peer-in display 45 so that the user may view left and right display screens inside the display 45 respectively with the user's left and right eyes. While viewing typically an image of the surgical site on a suitable viewer or display, the surgeon performs the surgical procedures on the patient by manipulating master control input devices, which in turn control the motion of robotic instruments.

The surgeon console 50 also includes left and right input devices 41, 42 that the user may grasp respectively with his/her left and right hands to manipulate devices (e.g., surgical instruments) being held by the robotic manipulator arm assemblies 120, 130, 140, and 150 of the patient-side cart 100 in preferably six or more degrees-of-freedom ("DOF"). Foot pedals 44 with toe and heel controls are provided on the surgeon console 50 so the user may control movement and/or actuation of devices associated with the foot pedals.

A processing device 43 is provided in the surgeon console 50 for control and other purposes. The processing device 43 performs various functions in the medical robotic system. One function performed by processing device 43 is to translate and transfer the mechanical motion of input devices 41, 42 to actuate their corresponding joints in their associated robotic manipulator arm assemblies 120, 130, 140, and 150 so that the surgeon can effectively manipulate devices, such as the surgical instruments. Another function of the processing device 43 is to implement the methods, cross-coupling control logic, and controllers described herein.

The processing device 43 can include one or more processors, digital signal processors (DSPs), field-programmable gate arrays (FPGAs), and/or microcontrollers, and may be implemented as a combination of hardware, software and/or firmware. Also, its functions as described herein may be performed by one unit or divided up among a number of subunits, each of which may be implemented in turn by any combination of hardware, software and firmware. Further, although being shown as part of or being physically adjacent to the surgeon console 50, the processing device 43 may also be distributed as subunits throughout the telesurgery system. One or more of the subunits may be physically remote (e.g., located on a remote server) to the telesurgery system.

Figure 3:
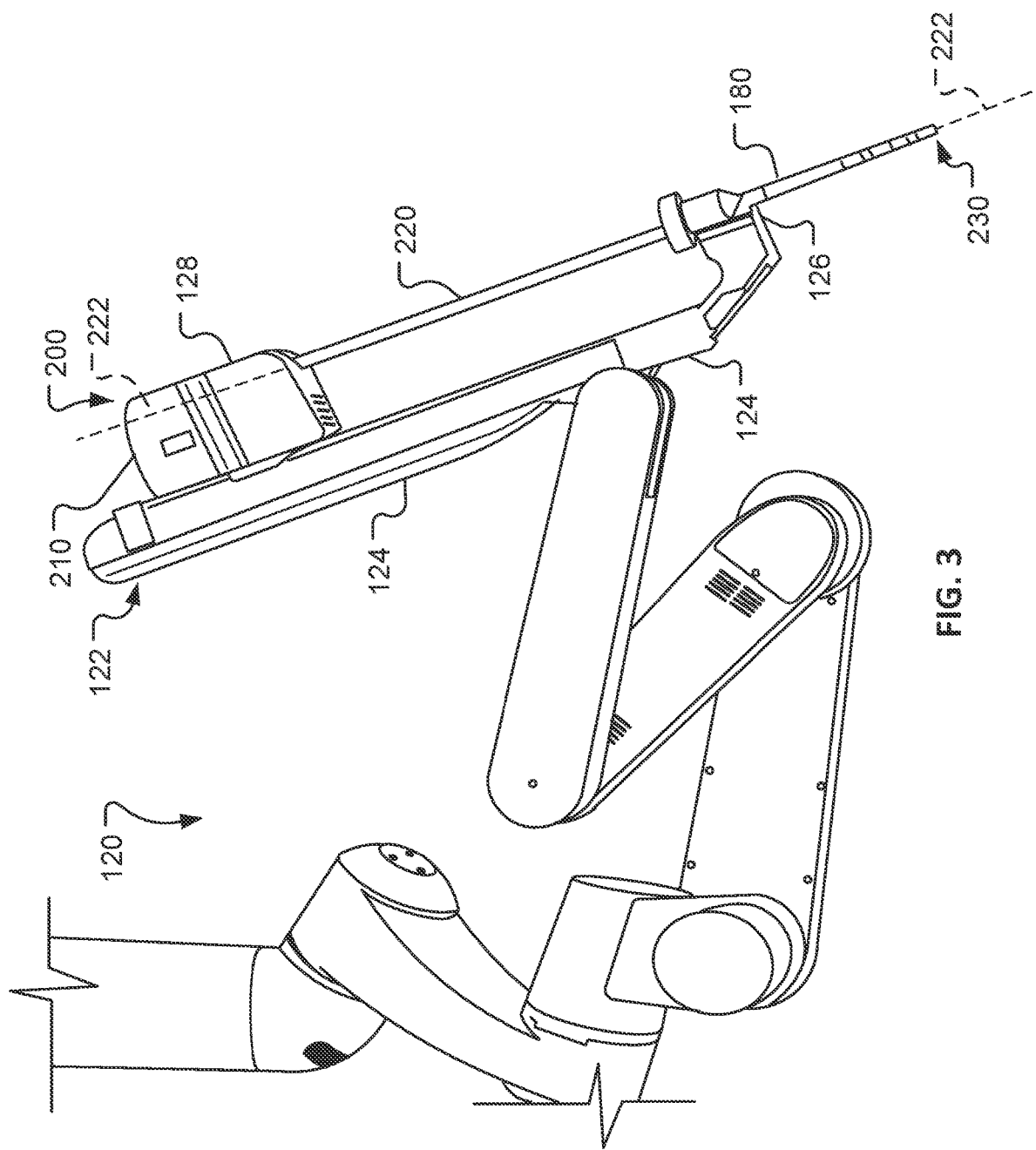
FIG. 3 is a side view of an example robotic manipulator arm assembly of a computer-assisted tele-operated surgery system.

Referring also to FIG. 3, the robotic manipulator arm assemblies 120, 130, 140, and 150 can manipulate devices such as an endoscopic stereo camera and surgical instruments to perform minimally invasive surgery. For example, in the depicted arrangement the robotic manipulator arm assembly 120 is pivotably coupled to an instrument holder 122. A cannula 180 and a surgical instrument 200 are, in turn, releasably coupled to the instrument holder 122. The cannula 180 is a hollow tubular member that is located at the patient interface site during a surgery. The cannula 180 defines a lumen in which an elongated shaft 220 of the endoscopic camera (or endoscope) or surgical instrument 200 is slidably disposed. As described further below, in some embodiments the cannula 180 includes a distal end portion with a body wall retractor member. The instrument holder 122 is pivotably coupled to a distal end of the robotic manipulator arm assembly 120. In some embodiments, the pivotable coupling between the instrument holder 122 and the distal end of robotic manipulator arm assembly 120 is a motorized joint that is actuatable from the surgeon console 50 using the processing device 43.

The instrument holder 122 includes an instrument holder frame 124, a cannula clamp 126, and an instrument holder carriage 128. In the depicted embodiment, the cannula clamp 126 is fixed to a distal end of the instrument holder frame 124. The cannula clamp 126 can be actuated to couple with, or to uncouple from, the cannula 180. The instrument holder carriage 128 is movably coupled to the instrument holder frame 124. More particularly, the instrument holder carriage 128 is linearly translatable along the instrument holder frame 124. In some embodiments, the movement of the instrument holder carriage 128 along the instrument holder frame 124 is a motorized, translational movement that is actuatable/controllable by the processing device 43. The surgical instrument 200 includes a transmission assembly 210, the elongated shaft 220, and an end effector 230. The transmission assembly 210 may be releasably coupled with the instrument holder carriage 128. The shaft 220 extends distally from the transmission assembly 210. The end effector 230 is disposed at a distal end of the shaft 220.

The shaft 220 defines a longitudinal axis 222 that is coincident with a longitudinal axis of the cannula 180. As the instrument holder carriage 128 translates along the instrument holder frame 124, the elongated shaft 220 of the surgical instrument 200 is moved along the longitudinal axis 222. In such a manner, the end effector 230 can be inserted and/or retracted from a surgical workspace within the body of a patient.

Laparoscopic surgery can entail the surgeon viewing the surgical site with the endoscope and performing fine motor manipulations with laparoscopic instruments for exploration, dissection, suturing, and other surgical tasks. These tasks often require fine bi-manual interactions with tissue. In some cases, such bi-manual motor tasks may generally be more easily performed when the surgeon is presented with a 3D view of the surgical scene. The surgical workspace within the body of a patient (the surgical scene) can be presented as a 3D visualization to the surgeon via the stereoscopic display 45. While the technology described herein primarily uses examples of a peer-in stereoscopic display, other types of stereoscopic and non-stereoscopic displays are also within the scope of the technology. A peer-in stereoscopic display refers to a display that allows a user to look into the display without having to wear it or simultaneously share it with another user. A stereo microscope can be an example of a peer-in stereoscopic device. The stereoscopic display 45, as illustrated in FIG. 2 is another example of a peer-in stereoscopic display.

In some implementations, a peer-in stereoscopic display 45 can include two display screens (one for each eye) each of which displays one of two images corresponding to a stereo pair images captured using a stereoscopic endoscope. Such stereo pair images, when displayed, causes a user to perceive depth in the displayed images. Stereo pair images can be captured in various ways including, for example, using two spatially separated cameras in a "dual camera" approach, collecting a light field in a plenoptic camera approach, or as described here in, using a dual pupil type device where two spatially separated apertures (also referred to as pupils) cause the capture of two slightly different images from two slightly different perspectives.

In the dual camera approach, two separate cameras and associated optics can be oriented such that they capture substantially the same scene from two locations separated by an 'inter pupillary distance'. This approach mimics human vision where two spatially separated eyes are used to capture a 3D view of the world. The orientation of the camera pair, at the time of acquisition, determines the orientation at which the images may be reproduced. For example, the cameras may be separated along a horizontal axis such that a view corresponding to a straight (or 'normal') head or an inverted head may be captured. However, for arbitrary angles of orientation of the two cameras, the horizontal distance between the cameras varies, thereby making the 3D presentation challenging. A camera pair with cameras facing the horizon separated in a plane perpendicular to gravity has fixed pupils and when rotated 90 degrees captures one image from above the other; this is not always the desired behavior.

In another approach, 3D scenes may be captured by sampling light fields, for example, using a plenoptic camera that captures both intensity and direction of some fraction of the many rays that pass through an optical system. Plenoptic cameras can include, for example, camera arrays, movable cameras, or cameras that contain lens arrays to sample the light field at some spatial and angular resolution. In this approach, it is possible to reconstruct, post-acquisition, synthetic camera views in which the depth of field may be manipulated to control the focus at different portions of the scene. Multi-view images may also be created in which the camera appears to move a small amount relative to the scene thus showing the depth in the acquired scene. These plenoptic systems may simulate the two views of a stereo pair by selecting the appropriate pencils of rays. Typically however, there is a substantial reduction in resolution in such systems that is undesired, as the information from most pixels is not used so those pixels are wasted.

In some implementations of a dual pupil type device, a single optical system can be used for both eyes. In some cases, a mechanical aperture can be moved from one location to another (e.g., from right to left) to allow light pass through two locations sequentially. If this is done at a sufficiently high rate, say 120 Hz, then a smooth sequence of stereo images may be acquired with a suitable high-speed camera. In stereoscopic endoscopes though, where the constraints on space and power resources can limit mechanical movements, implementing such a mechanical aperture may be challenging. The technology described herein provides for electronically controllable apertures that substantially avoids the drawbacks of mechanical apertures to realize a camera system suitable for incorporation in an endoscope. Further, by adjusting the location of the apertures based on an orientation of the endoscope, the technology facilitates 3D visualizations that may be perceived as natural, and thereby substantially improves the user experience of the surgeon during a surgical process. Using the technology described herein, image sequences are acquired using electronic shutters (e.g., based on activating/deactivating liquid crystal display (LCD) segments to pass/block light in an optical path) that may be synchronized to the display. This can result in the left eye observing the view through one pupil and the right eye observing the view through the other. Such split pupil cameras may therefore represent a simple light field camera in which only two views are sampled, and each at full resolution with no wasted pixels.

In some implementations, a stereo endoscope can include optics that are configured to look straight out the end of a tube or shaft housing a portion of the endoscope. Such endoscopes may be referred to as 0° endoscopes. However, in some cases, surgeons may also need endoscopes that look 'down' on their work area. For example, in laparoscopic surgery, this view is typically oriented at 30° with respect to the shaft of the endoscope. Endoscopes with other orientations (e.g., such as ones used in arthroscopy) are also possible; angles of view such as 45 and 70 degrees are also common.

Figure 4:
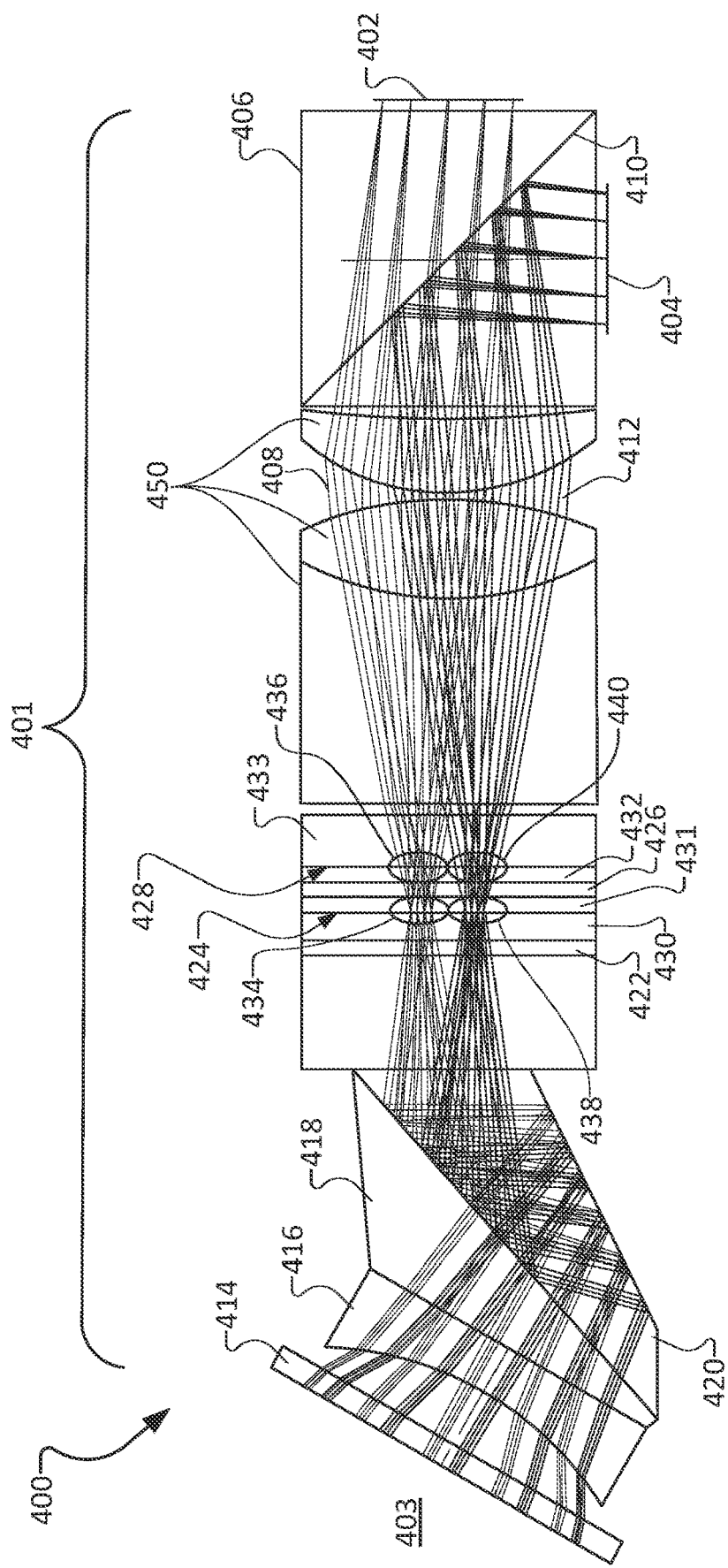
FIG. 4 is a schematic diagram illustrating optical paths through an example of a 30° stereoscopic endoscope.
Figure 11:
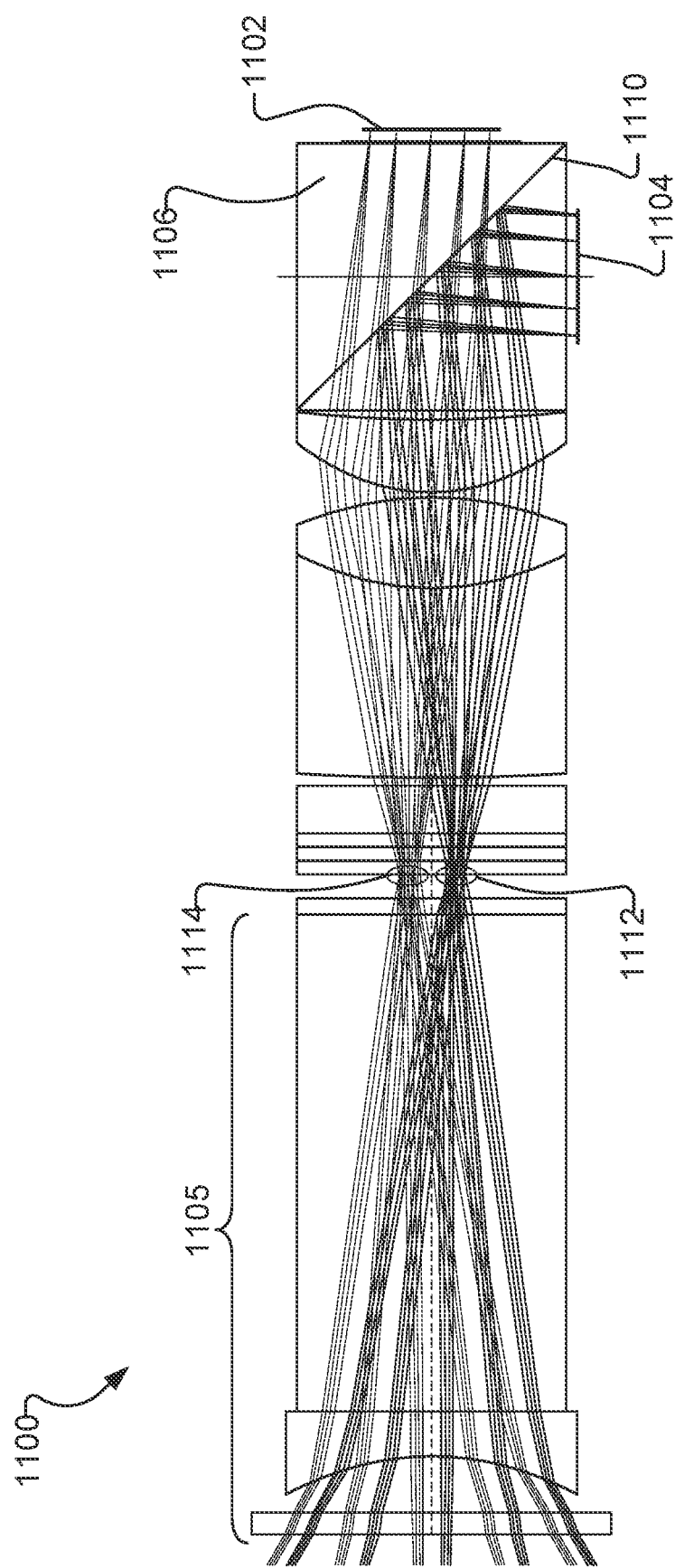
FIG. 11 is a schematic diagram illustrating optical paths through an example of a 0° stereoscopic endoscope with two sensors.

FIGS. 4 and 11 illustrate examples of a 30° endoscope and a 0° endoscope, respectively. Specifically, FIG. 4 is a schematic diagram illustrating optical paths of the invention through an illustrative simplified 30° stereoscopic endoscope 400, and FIG. 11 is a schematic diagram illustrating optical paths through an example of a 0° stereoscopic endoscope 1100. Referring to FIG. 4, the endoscope 400 includes an optical arrangement 401 of a plurality of lenses and other optical elements that direct light from a target imaging region 403 onto two image sensors 402 and 404, configured to sense the right view and the left view, respectively. In some implementations, the optical arrangement 401 includes a beam splitter 406 that allows a set of rays 408 to pass through the surface 410 while reflecting the set of rays 412 towards the image sensor 404. The surface 410 can be configured to reflect rays of one polarization state while allowing rays of a different polarization state to pass through. For example, the surface 410 can include a wire grid layer (such as developed by Moxtek Inc. of UT, USA, or Meadowlark Optics of CO, USA), which separates different linear polarization states through reflection and transmission. In some implementations, this facilitates acquiring the left and right images of the stereo endoscope substantially simultaneously in a compact form factor that avoids using larger diameter optics as may be needed for separate physical optical channels for the left and right images. One of the advantageous aspects of the technology described herein is that the left and right eyes match in performance as they use the same optical path. For example, if the optics 450 are moved longitudinally to focus the images on sensors 402 and 404, the left and right eyes will inherently match in terms of their respective focus curves. Additionally, aberrations due to tolerances in the optical system will also match between the images on the two sensors. This is beneficial for maintaining stereoscopic image quality.

In some implementations, the front end of the optical arrangement 401 can include a sapphire window 414, a front negative lens 416, a first portion 418 of a 30° prism, and a second portion 420 of the 30° prism. The 30° prism can include an air gap at the interface between the first portion 418 and second portion 420 such that light reflected from the surface of the second portion 420 is total internally reflected at the interface between the first portion 418 and second portion 420, as shown using the ray paths in FIG. 4. Some implementations may exclude the sapphire window 414, which is disposed to protect other portions of the optical arrangement 401.

In some implementations, the optical arrangement 401 includes two separate pupils or apertures defined in order to pass light corresponding to a right view and a left view, respectively. The two apertures may be defined by a combination of multiple optical elements such as one or more image transmission layers (e.g., liquid crystal layers), electrodes, and polarizers such that the apertures may be generated and blocked electronically, allowing for dynamic control over the location of the apertures. In some implementations, the apertures can be defined using a first polarizer 422, a first liquid crystal layer 424, a second polarizer 426 that is orthogonal to the first polarizer 422, and second liquid crystal layer 428. The first liquid crystal layer 424 can be energized using transparent electrodes disposed in a glass layer 430 adjacent to the liquid crystal layer 424, and complementary electrodes disposed in a glass layer 431 located on the opposite side of the liquid crystal layer 424 as compared to the glass layer 430. Similarly, the second liquid crystal layer 428 can be energized using transparent electrodes disposed in a glass layer 432 adjacent to the liquid crystal layer 428 and complementary electrodes disposed in a glass layer 433 located on the opposite side of the liquid crystal layer 428 as compared to the glass layer 432. The segments formed in liquid crystal layer 424 can be energized (as described below in more details) to form a right pupil or aperture 434 that allows light corresponding to the right view to pass through. The segments formed in liquid crystal layer 428 can be energized to define another region 436 that polarizes light from the pupil 434 in a way that it is transmitted through, as light 408, to the surface 410 of the polarizing beam splitter 406. The segments formed in liquid crystal layer 424 can also be energized to form the left pupil or aperture 438 that allows light corresponding to the left view to pass through. Correspondingly, the segments formed in liquid crystal layer 428 can be energized to define another region 440 that polarizes light from the pupil 438, light 412, in a way that it is reflected from the surface 410 of the polarizing beam splitter 406 towards the image sensor 404. The unwanted light (e.g., light that does not pass through the desired apertures may be absorbed by masks or the second polarizer 426). This description primarily uses a liquid crystal layer as an example of an image transmission layer. However, other electronically controllable image transmission layers (e.g., one that uses E-ink segments instead of liquid crystal segments) are within the scope of this disclosure.

Figure 5A:
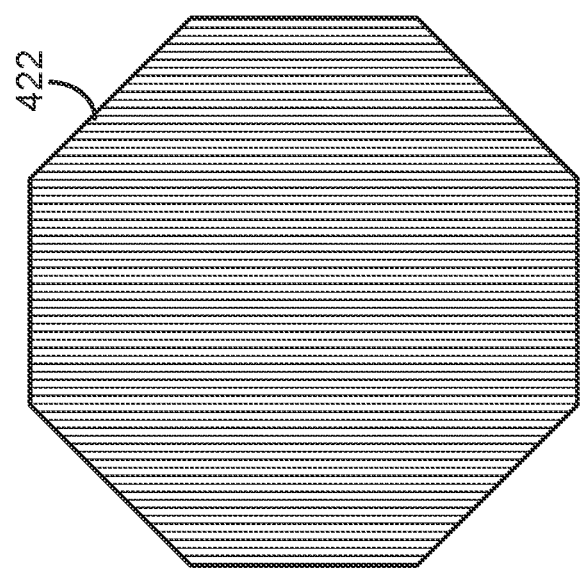
FIGS. 5A and 5B are schematic representations of examples of polarizers usable with the technology described herein.
Figure 5B:
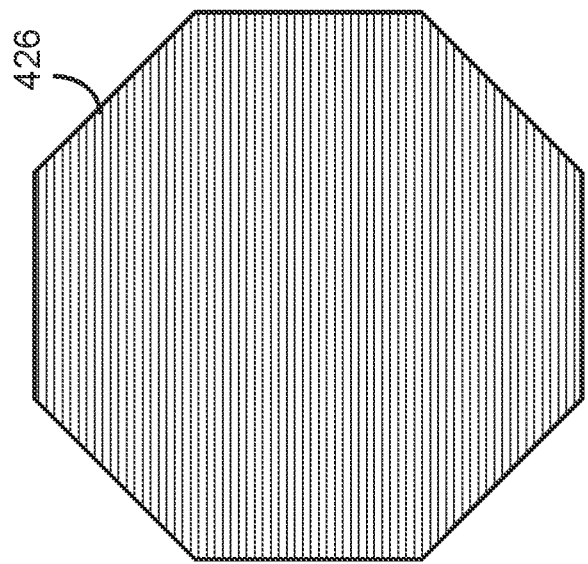

In some implementations, the liquid crystal element 428 rotates the light passing through the pupils 434 and 438 such that the light passing through the rotator pupil 436 is orthogonally polarized with respect to the light passing through the rotator pupil 440. In some implementations, the liquid crystal layer 424 can be segmented radially about an annular region and one or more of the segments may be used to define the pupil areas. The light emanating from both pupils defined on the liquid crystal layer 424 has the same polarization and traverses polarizer 426. Light not in the pupil areas is not rotated and is thus subject to the extinction ratio of two crossed polarizers 422 and 426. Example schematic (or symbolic) representations of such polarizers are shown in FIGS. 5A and 5B, respectively. In some cases, one could reverse these (possibly at the expense of a change in contrast ratio) and have polarizers 422 and 426 parallel to one another, and rotate the non-desired light.

Referring to FIG. 5A, in some implementations, the orientation of the polarizer 422 can be configured in accordance with the light source illuminating the surgical scene. For example, if the light source illuminating the surgical scene is polarized, the polarization direction and orientation of the polarizer 422 may be configured to be orthogonal to that of the light source, for example, to reduce the salience of specular reflections from the tissue surface. In some implementations, the polarizer 422 may incorporate a quarter wave plate together with a corresponding quarter wave plate on the illumination source to provide an orthogonality in circular polarization between the illumination and the imaging paths. In some cases, the polarizer 422 and or 426 may include or be augmented with compensation films in a similar fashion to those used on LCD displays to improve the angular performance and thus improving the system's contrast ratio by improving the transmission and extinction ratios of the liquid crystal pupil forming assembly.

Referring to FIG. 5B, the polarizer 426 can be configured to transmit light which is polarized appropriately and corresponds to the pupil areas defined using the liquid crystal layers. For example, the polarizer 426 can be configured to transmit light passing through the areas appropriately energized using the electrodes on the glass layers 430 and 432. Light passing through the non-energized areas may be absorbed, for example, by the combination of the polarizers 422 and 426, and one or more masking layers disposed to absorb the light. In some implementations, the polarization orientation of the polarizer 422 can be orthogonal to that of the polarizer 426. However, other relative polarization orientations of the two polarizers are also possible—for example, the "transmission" and "blocking" regions can be reversed and/or the polarizers parallel instead of crossed but those configurations are generally less optimal. In some implementations, the orientations can be dependent on the degree of retardation the liquid crystal layer 424 imparts.

Figure 6B:
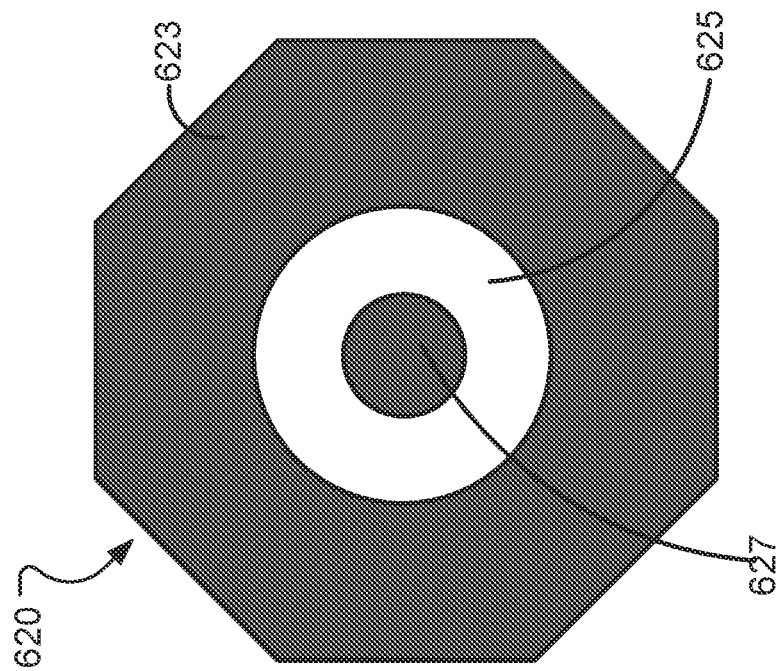
FIGS. 6A and 6B are examples of optical masks usable with the technology described herein.
Figure 6A:
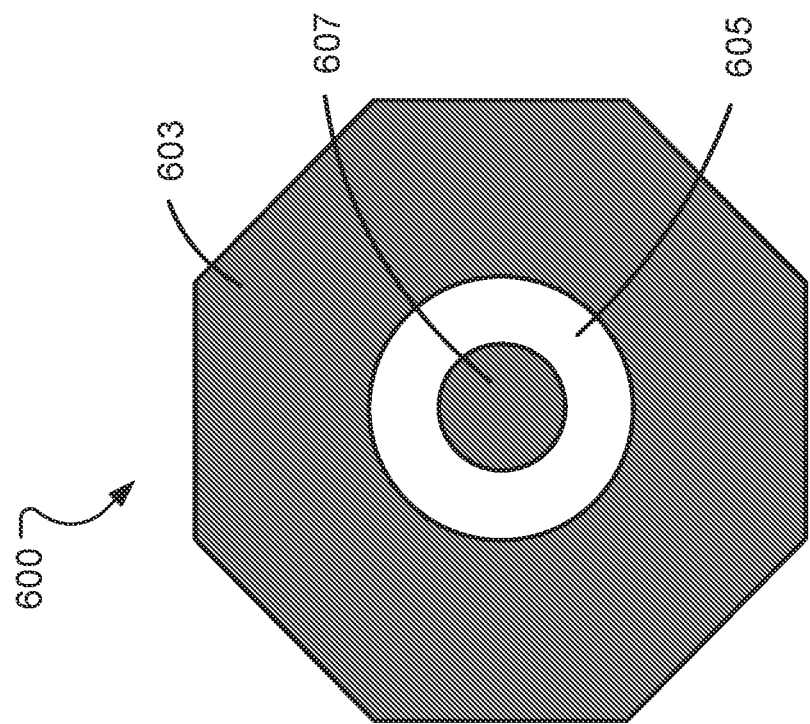

In some implementations, and preferably, a black mask may be disposed within the optical arrangement 401 to restrict light from passing through areas where a pupil is not going to be defined by the use cases of the device. An example of such a mask 600 is illustrated in FIG. 6A. In some implementations, the mask 600 can be formed by metal deposition, thin metallic masks, formed by semiconductor like processes, pad printed, or otherwise formed either on a glass surface or on the polarizer 422. In some implementations, the mask 600 may be implemented as a separate thin film (e.g. metal or Mylar) or glass plate. In the example shown in FIG. 6A, the area 605 is the transparent area and the area 603 is opaque or minimally transmissive. In this example, the area 607 is also opaque or minimally transmissive in accordance with the nature of the pupils. In some implementations, the diameter of the area 607 may be varied based on the pupil designs, and in some instances may be zero. In some implementations, the area 603 may be implemented on one layer (e.g., on the polarizer 422, or as an independent layer) and the area 607 may be implemented on a subsequent layer (e.g., the glass layer 430). These mask areas may be implemented in opaque thin foils or by deposition of chrome or like materials or by pad printing an ink or other or substantially black material in a thin layer.

In some implementations, the mask may also be located adjacent to the rotator pupils 436 and 440. In some implementations, a second mask adjacent to the rotator pupils can be used in conjunction with the mask 600. An example of such a mask 620 is shown in FIG. 6B. Because there may be a glass layer 432 between the pupils 434, 438 defining the liquid crystal shutters and the subsequent rotator pupils 436, 440, the rotator pupils 436, 440 can made be larger in area (as compared to the pupils 434, 438) to account for the angle of the light passing through the pupils. Accordingly, the mask 620 (FIG. 6B) can have a transparent region 625 that is larger than that of area 605 (FIG. 6A) to account for the light spreading between the two liquid crystal layers 424 and 428. Transparent region 625 is defined by dark areas 623 and 627. In some implementations, region 627 may not be present or be of vanishing diameter. In some implementations, compensation films may be used to increase the contrast ratio in resulting images.

In some implementations, instead of having two liquid crystal layers, the two apertures or pupils in a single layer may be polarized differently. For example, a polarizing element may be disposed before, at, or after each aperture in the optical path such that the two polarizing elements for the two pupils are orthogonal to each other. In some implementations, the two polarizing elements can be linear polarizers that are orthogonal to one another. In some implementations, the polarizing elements can include circular polarizers or colored notch filters.

Figure 7B:
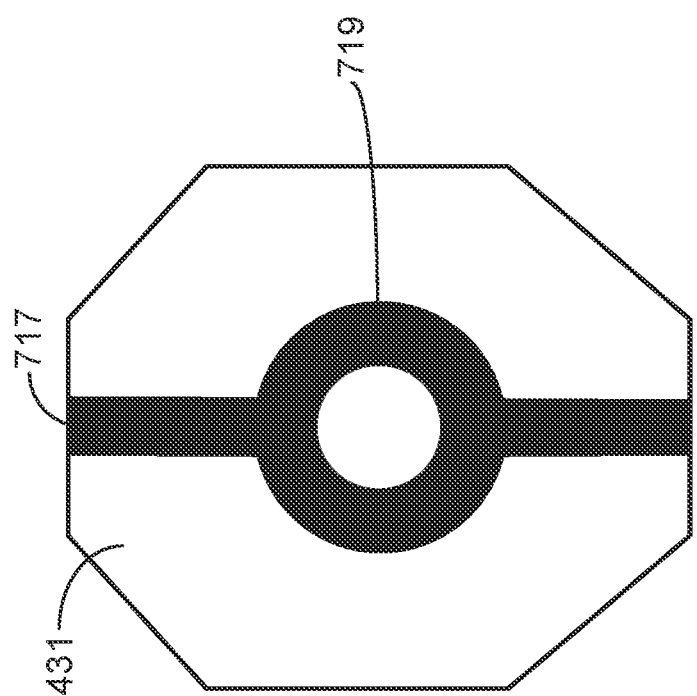
FIGS. 7A and 7B are example arrangements of electrodes usable in a first portion of a multi-pupil device in accordance with one implementation of the technology described herein.
Figure 7A:
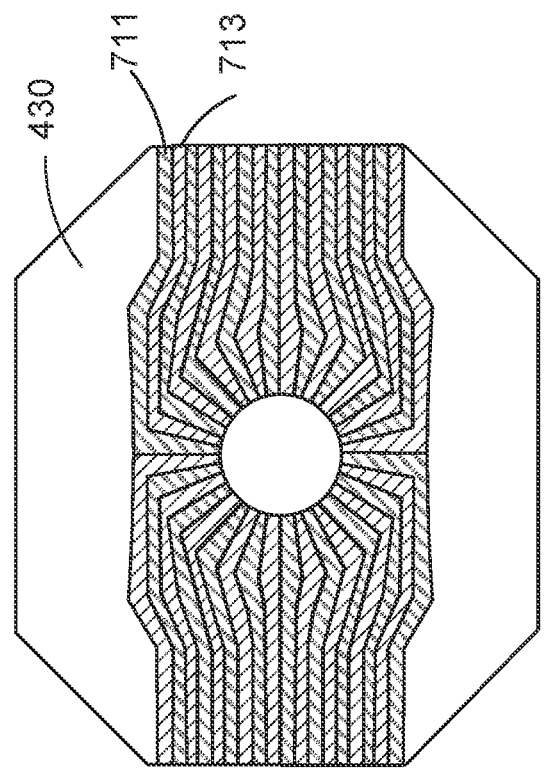

FIGS. 7A and 7B are example arrangements of transparent electrodes usable to control the pupil locations in the liquid crystal layer 424. Specifically, the FIG. 7A illustrates an example arrangement of transparent conductive electrodes disposed on the glass layer 430. The electrodes may be disposed on the surface of glass layer 430 that interfaces with the liquid crystal layer 424, and can be configured to control LCD segments forming the shutter pupils 434 and 438. The example of FIG. 7A shows a radial pattern of electrodes; with neighboring electrodes 711 and 713 being two of a plurality of electrodes controlling corresponding LCD segments defined in the liquid crystal layer 424. The neighboring electrodes are independent and are electrically isolated from one another. The electrodes can be coupled with electronic circuitry (not shown) using, for example, electrical contacts disposed near the edge of the glass layer 430. The electronic circuitry can be configured to drive the electrodes to activate/deactivate or energize/deenergize corresponding LCD segments.

FIG. 7B, illustrates an example arrangement of transparent conductive electrode disposed in the glass layer 431. The electrode may be disposed on the surface of glass layer 431 that interfaces with the liquid crystal layer 424, and in conjunction with the electrodes shown in FIG. 7A, can be configured to control LCD segments forming the shutter pupils 434 and 438. In the example shown in FIG. 7B, the electrode 717 is connected to the central region 719 that interfaces with the LCD segments in the liquid crystal layer 424. The electrode 717 can be connected to the electronic circuitry configured to control activation/deactivation of the LCD segments. In some implementations, at least a portion of the electronic circuitry may be disposed on the glass layer 431. The order of the electrodes may be reversed depending, for example, on the design constraints and the impact of edge effects at the segmented electrode. Also, in the particular examples shown, the octagonal shape of the layers 430 and 431 are elongated in orthogonal directions to facilitate the attachment of drive electronics to the transparent electrodes. In FIGS. 4 and 11, the octagonal and differential sizes of layers 430 and 431 are not shown (symmetrical round parts are shown) as the electronic requirements do not impact the optically relevant features emphasized in these figures.

Figure 8B:
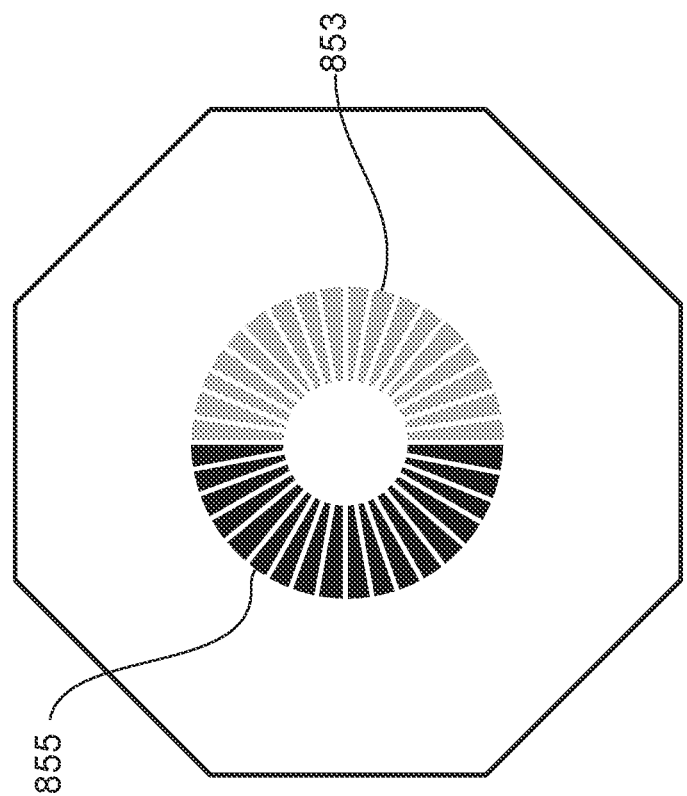
FIG. 8B is an example of rotator segments created with the combination of electrode arrangements of FIGS. 7A, 7B, and 8A.
Figure 8A:
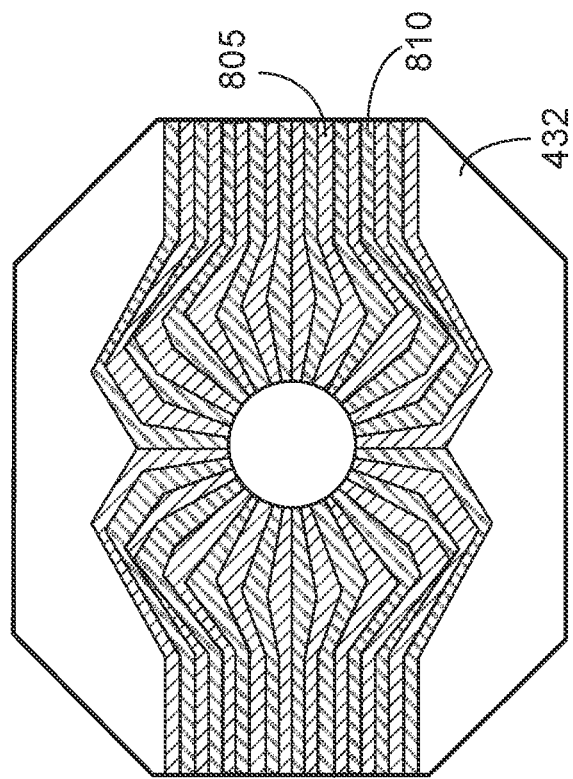
FIG. 8A is an example arrangement of electrodes usable in a second portion of the multi-pupil device of FIG. 7A.

FIG. 8A is an example arrangement of electrodes usable for controlling the rotator regions 436, 440. The transparent electrodes can be disposed on the glass layer 432 to impart appropriate polarization to the light passed through the two pupils 434 and 438 formed in the liquid crystal layer 424. The light that passes through the glass layer 432 is polarized by the second polarizer 426. In some implementations, the glass layer 432 includes a radial pattern of electrodes such as the electrodes 805 and 810. Neighboring electrodes are independent, electrically isolated from one another, and coupled to the electronic circuitry configured to control the operations of the electronic pupils. The electrodes are driven by electronics conductively attached at the perimeter of the glass. In some implementations, the electrode segments disposed on the glass layer 432 are larger in outer radius and smaller in inner radius in comparison to the electrode segments disposed in the glass layer 430 (as shown in FIG. 7A), to account for light that passes through the glass layer 430 at an angle. In some implementations, the configuration of the electrodes disposed in the glass layer 432 can be substantially identical to the configuration of the electrodes disposed in the glass layer 430, at the potential cost of introducing vignetting on the inner and outer edges of the annular aperture segments. This may be alleviated, for example, by using a mask 600 (FIG. 6A) that is radially undersized relative to the electrode array and using a mask 620 (FIG. 6B) that is radially enlarged.

FIG. 8B is an example of candidate rotator segments created in the liquid crystal layer 428 with the combination of electrode arrangements of FIGS. 7A, 7B, and 8A, 8C. The liquid crystal cells or amalgamation of segments 853 and 855, and the intervening liquid crystal layer form a device that can rotate the polarization of incoming light into two orthogonally polarized states, respectively. In some implementations, the segment 853 may polarize the light from one pupil in such a way that the light is orthogonally polarized with respect to the light from the other pupil passing through the segment 855. For example, the two groups of segments (as depicted by two different shades) shown in FIG. 8B may represent segments that rotate the polarization of the light by 90°, and segments that let the light pass effectively unrotated, respectively.

Figure 8C:
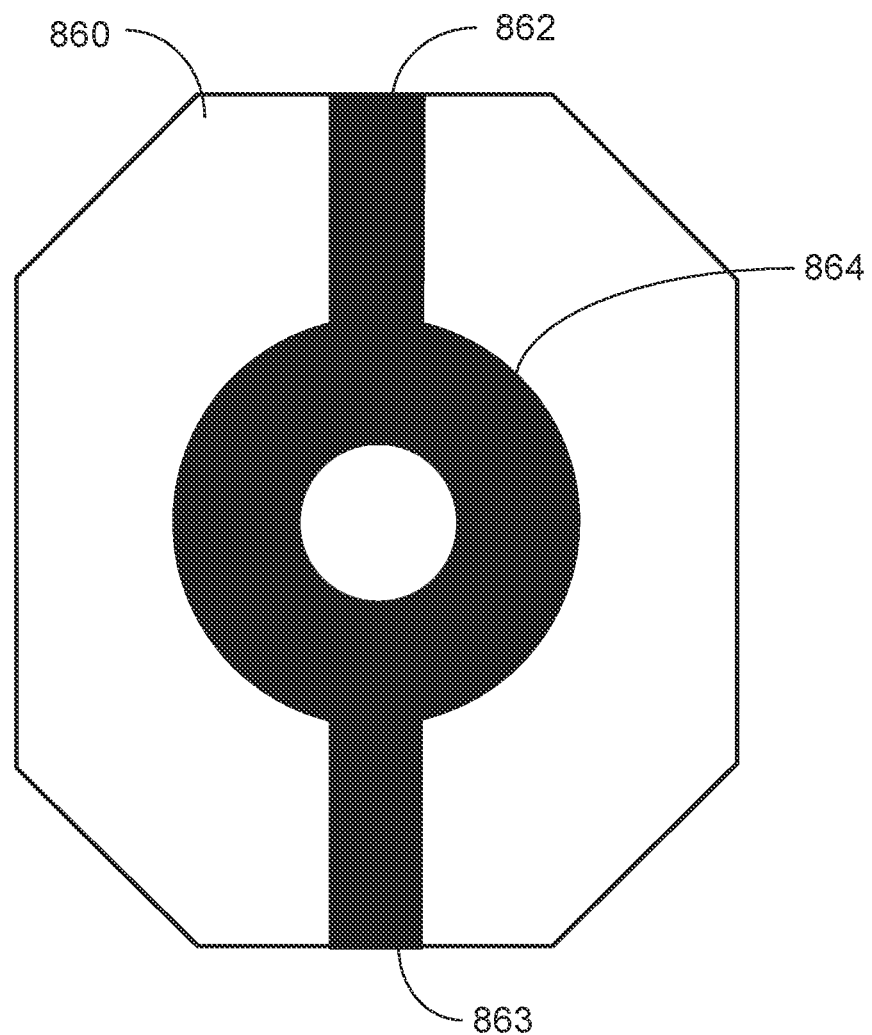
FIG. 8C is an example of the electrode used in conjunction with those in 8A to create patterns of polarization control as illustrated in 8B.

FIG. 8C is an example of a transparent electrode that can be used in conjunction with the segments shown in 8A. The liquid crystal material 428 (a typical twisted nematic (TN) type for example) can be disposed between the electrodes shown in FIGS. 8A and 8C. A portion of the transparent electrode 864 can be configured to face the segments shown in FIG. 8A such that the portion faces the electrode areas 805, 810 to form the liquid crystal cells or segments (such as ones that may be found in the LCD display of a digital watch). While the example of FIG. 8C (and those in other figures) show the electrode as a dark shaded portion, in practice the electrode layers can be substantially transparent, and constructed from a transparent conductive material such as indium tin oxide (ITO). The active electrode area 864 can be driven by electronics attached to the electrode, for example at locations 862 and/or 863. The electronics may be interfaced at the locations 862, 863 using various techniques such as ones using conductive adhesives, metallic clips, or zebra type connectors. By electronically controlling the voltage on the electrode area 864 and the voltages on the electrodes of FIG. 8A, and creating controlled voltage differences between the electrode area 864 and selected segments of FIG. 8A, patterns of polarization rotation can be imparted on the light traversing the liquid crystal cell. Examples of segments supporting the patterns are shown in FIG. 8B.

Figure 9B:
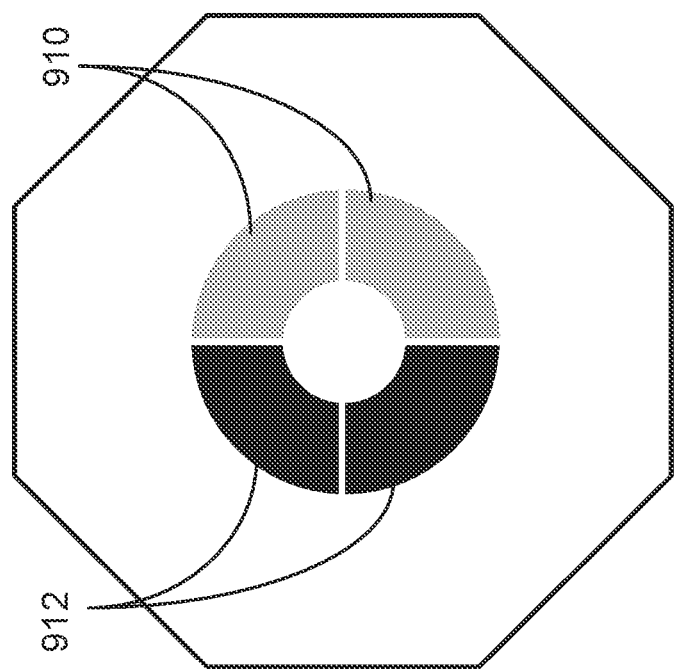
FIG. 9B is an example of rotator segments created with the combination of electrode arrangements of FIGS. 7A, 7B, and 9A
Figure 9A:
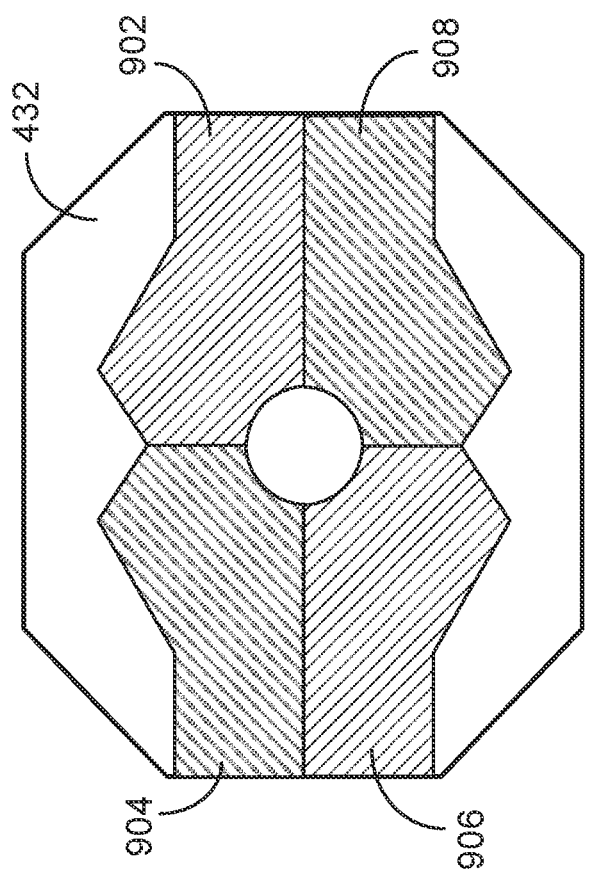
FIG. 9A is another example arrangement of electrodes usable in a second portion of the multi-pupil device of FIG. 7A.
Figure 9C:
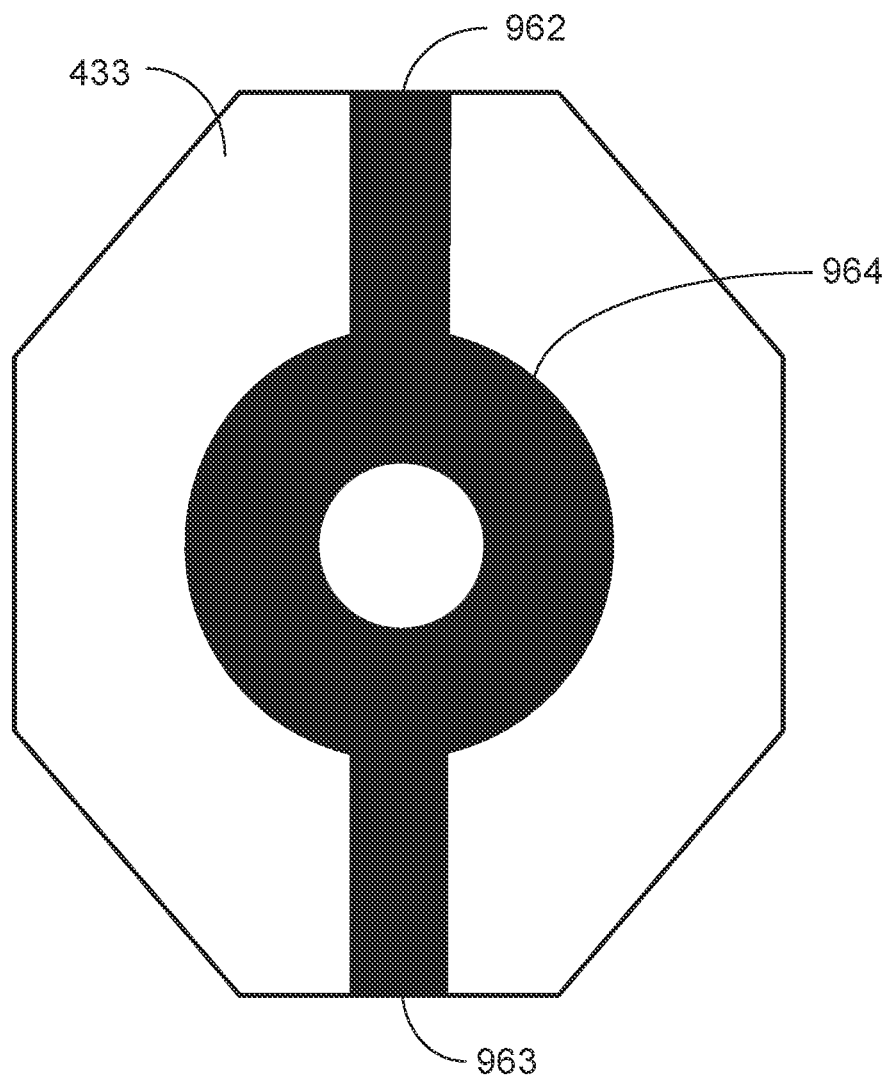
FIG. 9C is an example of the electrode used in conjunction with those in 9A to create patterns of polarization control as illustrated in 9B

Referring again to FIG. 8A, the electrode segments disposed on the glass layer 432 have similar radial angles as that of the pupil forming electrodes disposed in the layer 430 (as shown in FIG. 7A). However, other configurations are also possible. In some implementations, the electrode segments disposed in the glass layer 432 may have a coarser resolution. For example, pupils that are known a-priori to be disposed at substantially 180° with respect to each other may be implemented using only four electrode segments in the glass layer 432. This is shown using the examples of FIGS. 9A, 9B, and 9C. Specifically, FIG. 9A is another example arrangement of electrodes to form the four segments 902, 904, 906, and 908. FIG. 9C shows an example of a transparent electrode to complete the liquid crystal cells. The liquid crystal material 428 is interposed between the electrodes shown in FIGS. 9A and 9C. The transparent electrode area 964 is disposed on the glass layer 433. The electrode is driven by connection through one or both of the locations 962, 963, which connect to the drive electronics. Thus the segments 902, 904, 906, and 908 when electrically controlled together with the electrode area 964, can yield the pattern shown in FIG. 9B. In some implementations, light passing through rotator segments 910 is orthogonally polarized to that passing through rotator segments 912. Thus, polarization control is achieved with the electrical manipulation of the first 424 and second 428 LCD layers. The electrode shown in FIG. 9C is used in conjunction with those in FIG. 9A to produce the rotator segments illustrated in FIG. 9B. In the example of FIG. 9B, the rotator segments 910 impart one type of polarization while the rotator segments 912 impart a different type of polarization (e.g., polarization that is orthogonal with respect to the polarization imparted by the rotator segments 910). In some implementations, the four rotator segments illustrated in FIG. 9B may be sufficient to maintain a 180° separation between the pupils 434 and 438. Naturally, other numbers of segments are possible, and the examples shown are illustrative.

Referring again to FIG. 4, a surgeon may wish to be able to rotate the shaft of the 30° endoscope 400 to look at the sides of the cavity. In such cases, a pair of statically defined pupils will end up being located one above the other, or in some other arbitrary position, where the horizontal separation needed for the corresponding stereo images is lost. The technology described herein allows for dynamically defining the pupils using the LCD segments such that the pupil locations adapt to the rotation of the endoscopic camera 400. During a rotation, or a rolling motion, the endoscope sees a different view relative to gravity and the pupils may be progressively adjusted as described to keep the camera's left and right eyes separated correctly relative to the horizon. Correspondingly, the images from the image sensors can be electronically rotated to keep the orientation of the image displayed from the sensor oriented as desired on the display screen. In some implementations, a circular image may be presented to the surgeon.

Figure 10B:
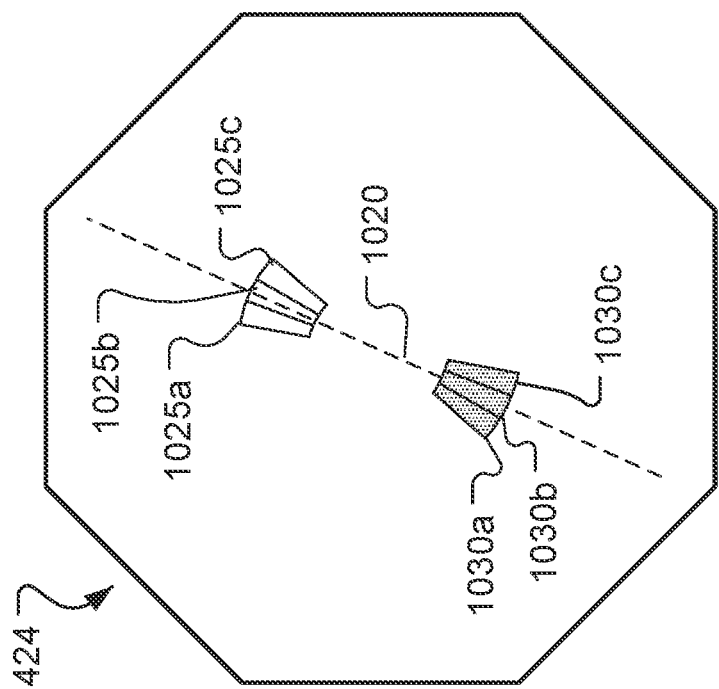
FIGS. 10A and 10B are examples of pupil positions for two different orientations of a stereoscopic endoscope, respectively.
Figure 10A:
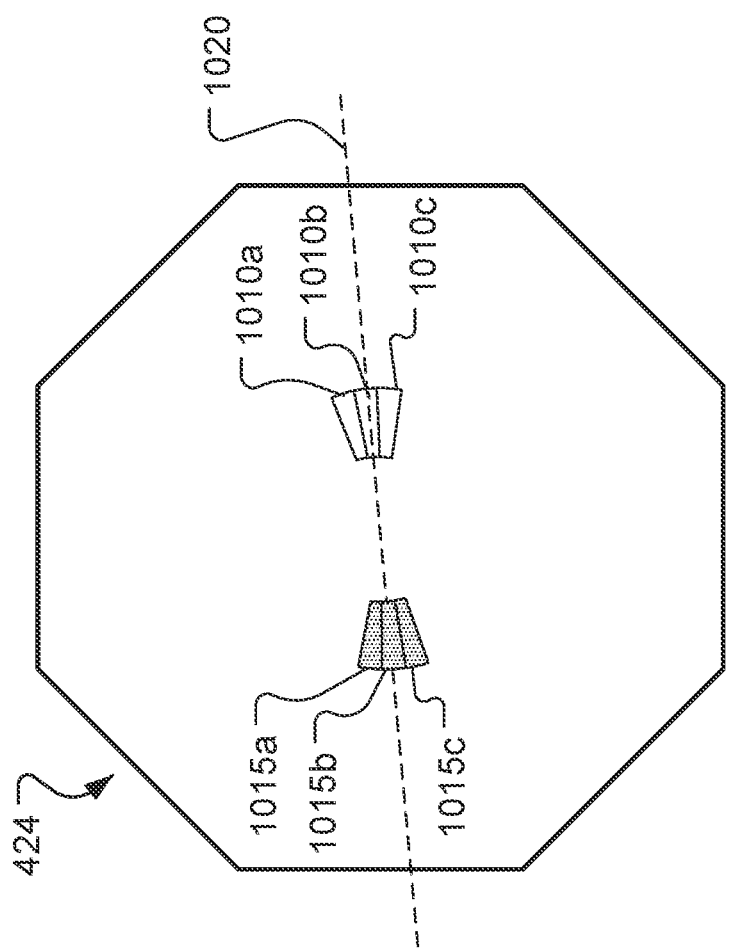

FIGS. 10A and 10B are examples of pupil positions for two different orientations of a stereoscopic endoscope, respectively. In the examples of these figures, the two pupils 434 and 438 are formed in the liquid crystal layer 424 by energizing six LCD segments using corresponding electrodes (FIG. 7A) defined on the glass layer 430 in conjunction with the electrode 717 disposed on the glass layer 431. Specifically, the segments 1010*a*, 1010*b*, and 1010*c* (1010, in general) are energized to define the pupil 438, and the segments 1015*a*, 1015*b*, and 1015*c* (1015, in general) are energized to define the pupil 434. Note that while the energized segments are shown in a dark shade, with the other segments being white, this is for illustration purposes only; as is known to one in the art, the liquid crystal appears transparent in both states and only becomes 'dark' between appropriately oriented polarizers. In practice, the shaded segments would be energized such that they become substantially transparent and allow light to pass through, while the rest of the segments are held at the other state to hinder light from passing through polarizer 426. Also, while the example of FIG. 10A shows three segments per pupil, more or less number segments may be used for each. Using more segments for each pupil would increase the corresponding aperture's effective diameter (potentially improving light throughput) but reducing the effective inter pupillary distance, as measured by the distance between the centroids of the two regions 1010 and 1015.

In the example of FIG. 10A, the stereoscopic endoscope is oriented at a particular angle with respect to a reference orientation, as defined, for example, by the axis 1020 connecting the LCD segment 1010*b* and 1015*b*. In some implementations, the axis 1020 may represent the "horizon"; i.e., an orientation that is perpendicular to the direction of the earth's gravity. However, other reference orientations are also possible. For example, the orientation of the surgeon's eyes relative to a large display mounted on the wall or a boom can be measured, and the position the pupils of the endoscope may be adjusted substantially similarly such that the surgeon's stereo perception remains accurate, even if the surgeon's head is tilted relative to the display. Making the pupil positions adaptive to the surgeon's head orientation may particularly improve the surgeon's user-experience in some cases; for example, in laparoscopic surgery situations where the location for the surgeon's hands may dictate a non-ideal body pose relative to the display.

If the endoscope is rotated to another angle, such as in the example shown in FIG. 10B, the axial orientation of the endoscope changes with respect to the reference orientation represented by the axis 1020. In such cases, to maintain the same angle of orientation, relative to gravity, for the pupils 434, 438, as in the case of FIG. 10A, different sets of LCD segments may need to be energized. In the example of FIG. 10B, the LCD segments 1025*a*, 1025*b*, and 1025*c* (1025, in general) are energized to define the pupil 438, and the segments 1030*a*, 1030*b*, and 1030*c* (1030, in general) are energized to define the pupil 434. Therefore, to maintain the angle of orientation across multiple endoscope orientations, the aperture locations corresponding to the pupils are determined to maintain a predetermined spacing between the first and second aperture locations, and the apertures are then created at the new locations by energizing the corresponding LCD segments. While the examples in FIGS. 10A and 10B show a liquid crystal layer with radial LCD segments, other arrangements of such segments are also possible. Additionally, the predetermined distance requirement is somewhat arbitrary in the general case and could be changed in systems using the patterns shown in FIGS. 7A, 7B and 8A, 8C. The pattern shown in FIGS. 9A and 9C illustrates a 180 degree separation.

Figure 10D:
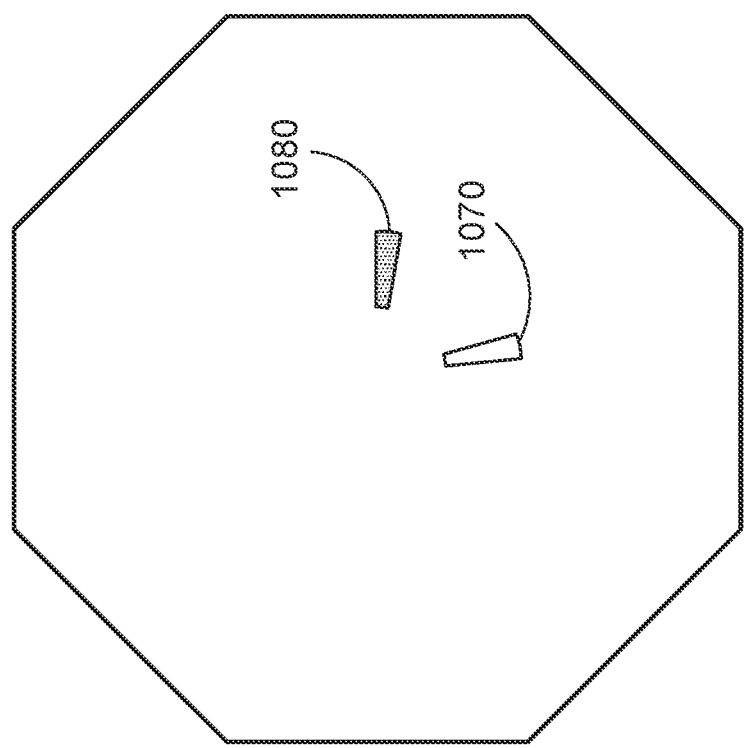
FIGS. 10C and 10D illustrate examples of different configurations and positions of the pupils.
Figure 10C:
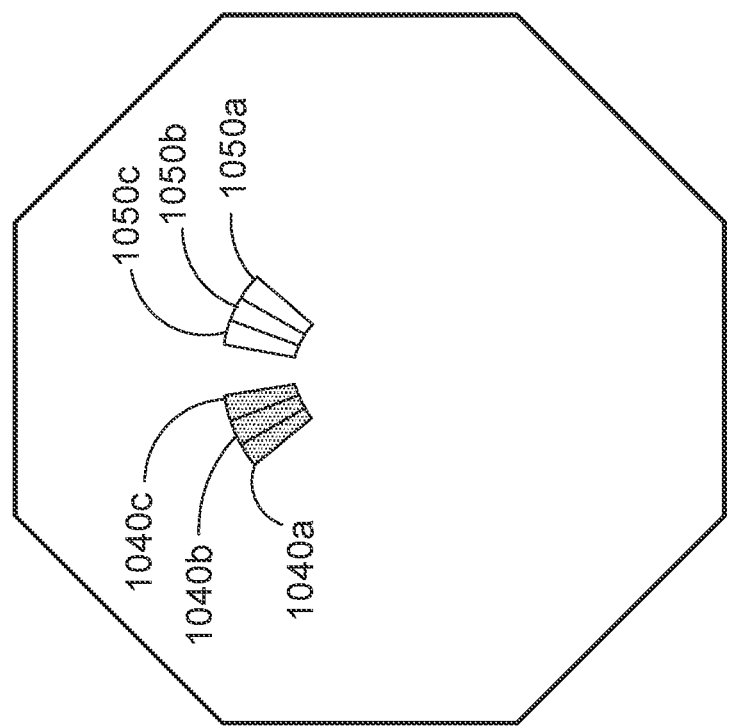

In some implementations, it may be desirable to be able to change the distance between the pupils and change their relative orientation. FIG. 10C illustrates two pupils formed by controlling the segments in the two LCD layers. In this case, the pupils are not separated by 180 degrees. In this case, segments 1040a, 1040b, 1040c form one pupil and segments 1050a, 1050b, 1050c form the second. These pupils, by the described operation of the LCD layers are orthogonally polarized and would form images, in the configuration of FIG. 4, on sensors 402 and 404. Pupil separation and size may be controlled, FIG. 10D shows the pupils moved and changed in size. 10D shows pupils 1070 and 1080 which are orthogonally polarized and in a different configuration as compared to that shown in FIG. 10C. Pupils may be moved in orientation and or relative position based on control signals which come from control signals (e.g., physical or in software) calculated from the images acquired by the endoscope or some other source. For example, the pupil spacing might be dynamically controlled based on the distance from the endoscope to the surgical site for example.

While the description above primarily uses the example of the 30° endoscope 400 shown in FIG. 4, the technology may also be used for other endoscopes such as a 0° endoscope. FIG. 11 is a schematic diagram of an example of a 0° endoscopic camera 1100, which includes two sensors 1102 and 1104. The endoscope 1100 may be substantially similar to the endoscope 400 described with reference to FIG. 4, except that the 0° endoscope includes the lens arrangement 1105 instead of the 30° prism of the endoscope 400. The technology described above with reference to the 30° endoscope 400 can be extended for the endoscope 1100 to control the locations of the pupils 1112 and 1114 such that the corresponding captured light can be separated using the polarizing beam splitter 1106 with appropriate coating or wire grid polarizing layer on surface 1110 separating the two orthogonal polarizations so as to capture the stereo images using the sensors 1104 and 1102, respectively. The selection of which pupils are used allows the 0 degree endoscope to rotate electronically without using moving parts—for example, the pupils can be rotated as described, and the images rotated electronically (or in software). From the user's perspective, this can have the effect of appearing to rotate the stereo camera system. This ability could also be used by machine vision algorithms for calculating characteristics of the surface being observed, calculating distance, and surface normals for example.

In some implementations, the electronic pupil control described herein may also be used to capture stereo images sequentially, using a single image sensor. For example, the two pupils corresponding to the left image and right image may be created sequentially, and the corresponding images may be captured using a single sensor in a time-division multiplexed arrangement. FIG. 12A is a schematic diagram illustrating an example of a 0° stereoscopic endoscopic camera 1200 that uses one sensor for sensing both stereoscopic images. In this approach, light from a surgical scene 1202 enters the endoscope 1200 through the lens arrangement 1105. In some implementations, the lens arrangement 1105 can include a first polarizer to polarize the incoming light. The optical path of the light through the endoscope 1200 is represented by example sample rays 1206 passing through the right pupil 1207 and example rays 1208 passing through the left pupil 1209. In some implementations, the glass layer 1210 can be thicker as compared to the corresponding layer 430 in the endoscope 400 (FIG. 4) to support thinner cell geometries for ferroelectric liquid crystal materials, which may be used for fast switching of LCD segments defining the pupils. In some cases, the thick glass layer 1210 provides more stability and stiffer mechanical support, making it potentially easier to create and maintain thin cells for such materials. In some implementations, the ferroelectric liquid crystal material can be selected to facilitate fast switching (e.g., once every 5 ms, 2 ms; 100 µs, or less).

The ferroelectric crystal material can be disposed as a thin layer (e.g., of width of a few µm) between active electrodes disposed on glass (or other transparent substrate) layers. In some implementations, the ferroelectric liquid crystal layer can be configured to let linearly polarized light pass through effectively unchanged, or, responsive to electronic control, be rotated by 90°. In some implementations, the light passing through the first pupil may be polarized differently from the light passing through the second pupil, for example, as described above with reference to FIG. 4. In some implementations, light from both the left and the right pupils are polarized the same way and are transmitted by a second polarizer. Light passing through the second polarizer then passes through optics 1212, which unlike the endoscope 1100 (FIG. 11), does not include a beam splitter 1106. Rather the light from the right pupil (represented by the rays 1214) as well as the left pupil (represented by the rays 1216) pass through the optics 1212 to reach the image sensor 1218. In some implementations, pad printed black masks or some other light blocking elements may be incorporated in the optical path, for example, to help improve the contrast ratio of the image sensed by the image sensor.

In implementations where the light from both the right pixel and the left pixel are sensed by the same sensor, the two corresponding images can be sensed in different ways. FIG. 12A shows an implementation where the light from the two pupils are polarized in different ways, and corresponding polarizers can be used in the image sensor 1218 to differentiate between the corresponding images. FIG. 12A shows an expanded version of a portion 1220 of an example image sensor 1218. The portion 1220 includes multiple pixels wherein a polarizer is overlaid on each pixel. The polarizers for the pixels in a first set are different from the polarizers for the pixels in a second set, such that the pixels in the first and second set can selectively sense light with corresponding polarization states. In the example shown in FIG. 12A, the polarizer for pixel 1224 is orthogonal with respect to the polarizer for the pixel 1226. Therefore, the image sensor can be configured to sense light from the two pupils simultaneously if the light from the pupils are appropriately polarized and match the pixelated polarizer at the image sensor 1218.

Figure 12B:
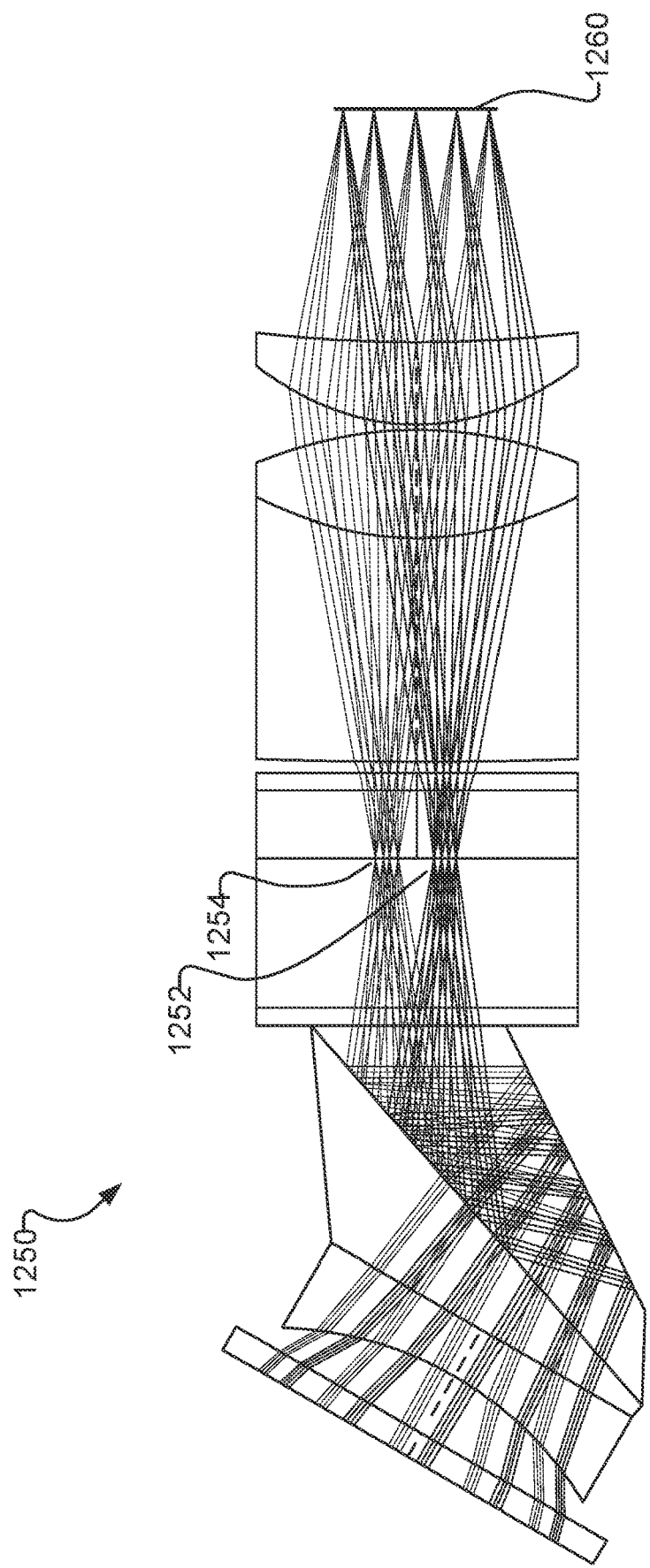
FIG. 12B is a schematic diagram illustrating optical paths through an example of a 30° stereoscopic endoscope that uses one sensor for sensing both stereoscopic images.

In the example of FIG. 12A, a subset of the pixels of the sensor 1218 sense the light from the right pupil, and a different subset of the pixels sense the light from the left pupil. Therefore, the spatial resolution of each eye image is less (half) than that afforded by the sensor 1218. In some implementations, the full spatial resolution of the image sensor 1218 can be used to sense the two images by using the sensor for each pupil sequentially on a time division multiplexed basis. This is illustrated in FIG. 12B using the example of a 30° endoscope with one image sensor 1260. In this example, the electronic circuitry controlling the state of the pupils 1252 and 1254 are synchronized, for example, with the timing signals controlling the frame rate for the sensor 1260. In the case of a sensor with a global shutter, which pupil is active alternates at each frame boundary. Thus, the left pupil 1252 is open (and the right pupil 1254 is dark) when a left image is being acquired. Similarly, the right pupil 1254 is open (and the left pupil 1252 is dark) when a right image is being acquired. This sequence can be repeated to acquire stereo images at the spatial resolution afforded by the sensor 1260, but at the cost of a lower frame rate for the stereo images. For example, if the imager frame rate is 60 Hz, then a stereo pair is acquired at 30 Hz although a 'new' image is acquired at the rate of 60 Hz. In another example, if the imager is run at a frame rate of 120 Hz, a stream of stereo images at 60 Hz can be generated.

Figure 13:
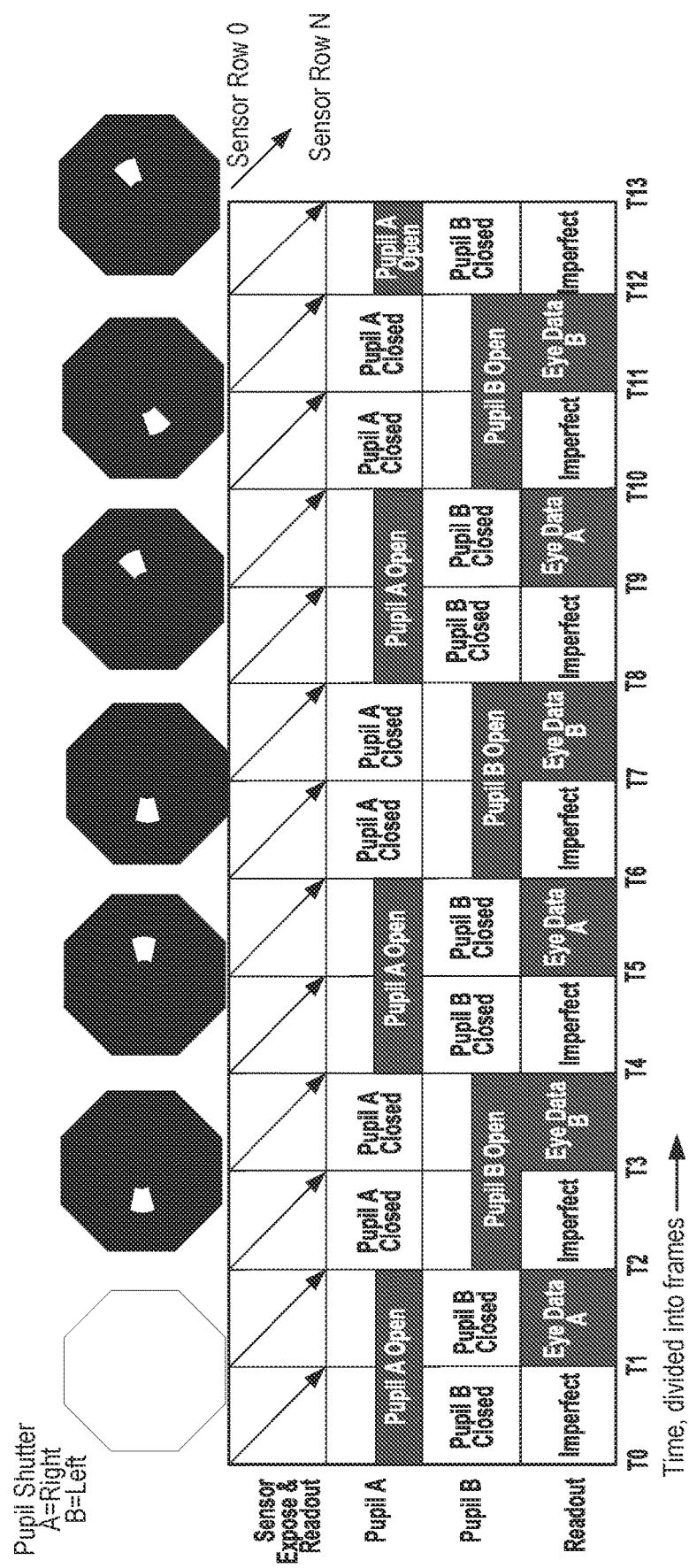
FIG. 13 is a schematic diagram illustrating a process of sensing both stereoscopic images using a single sensor with a rolling shutter.

In some implementations, if the sensor 1260 employs a rolling shutter, the exposure time and readout for the two pupils may overlap, and thus need to be accounted for. An example of such a scenario is illustrated in FIG. 13. In the example shown, each pupil is 'open' for two consecutive time units synchronized with the frame boundaries. During the second of those two time units (each of which may also be referred to as a frame time), the data corresponding to the pupil with the open shutter is acquired. The readouts marked 'imperfect' in FIG. 13 are images where the illumination on the sensor is not correct, and hence the data corresponding to the readouts are discarded. Therefore, the rate of acquisition of the stereo pairs in such an arrangement is one fourth of the underlying frame rate. For example, if the frame rate is 240 Hz, stereo pairs are acquired at 60 Hz. In some implementations, because the data acquisition for one pupil is complete before that for the other pupil, a sequential display arrangement can be used to reduce end-to-end latency of the system. In some implementations, if the surgeon's head is moving, for a 240 Hz frame rate, the pupil positions can be updated at 120 Hz rather than 60 Hz, to potentially improve the system response under fast head motion. For example, the images for left and right pupils may be acquired at subsequent moments in time and as such, the pupils may be placed in the ideal positions for each eye. In some implementations, the pipelined nature of the arrangement illustrated in FIG. 13 provides reduced latency and resource related advantages due to frames being processed sequentially rather than simultaneously.

Figure 14:
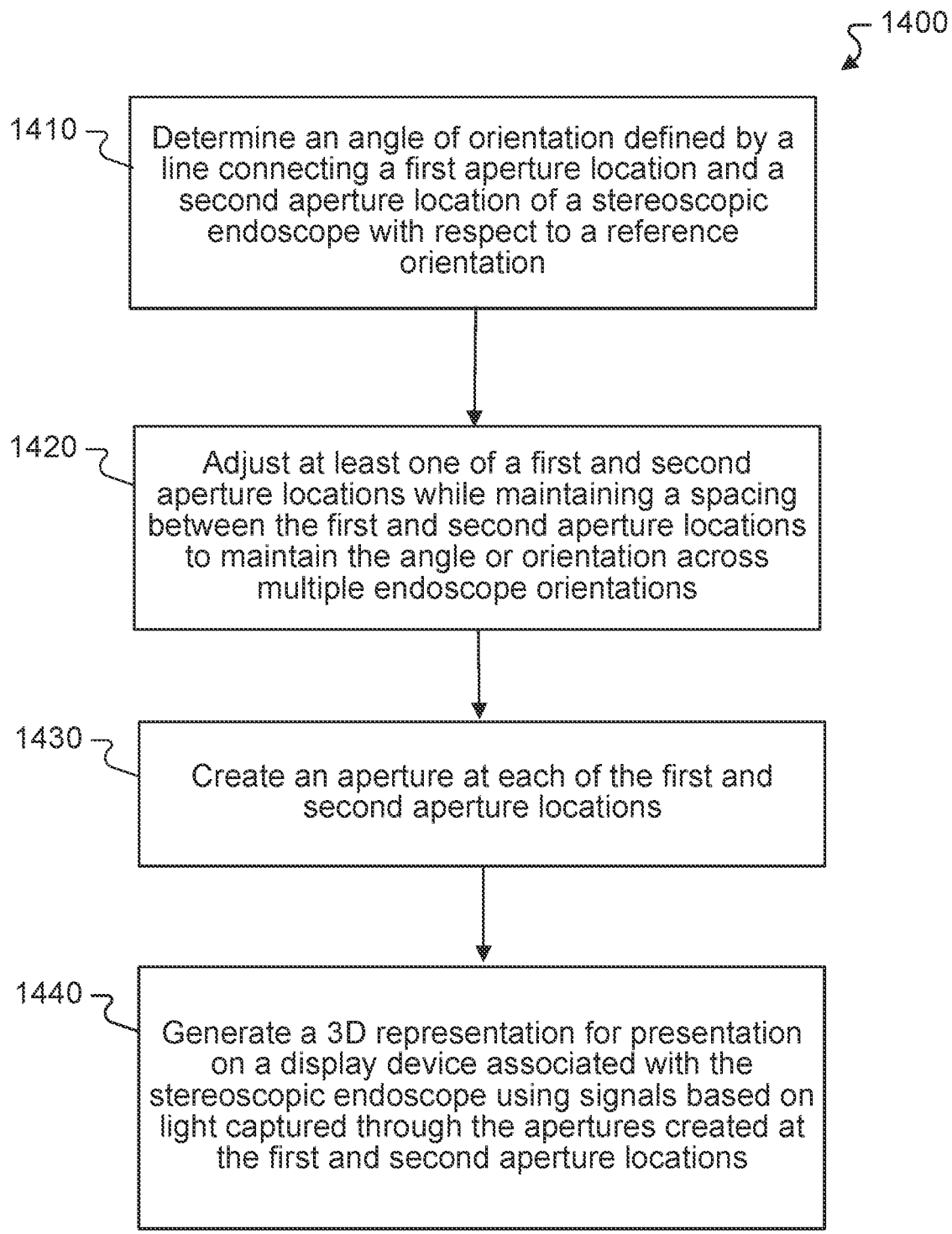
FIG. 14 is a flowchart of an example process for generating a 3D representation using technology described herein.

FIG. 14 is a flowchart of an example process 1400 for generating a 3D representation using technology described herein. In some implementations, operations of the process 1400 can be executed, at least in part, by the processing device 43 described above with reference to FIG. 2. In some implementations, operations of the process 1400 may be executed by one or more processing devices of an endoscope such as the endoscopes 400, 1100, 1200, or 1250 described above. Operations of the process 1400 includes determining an angle of orientation defined by a line connecting a first aperture location and a second aperture location of a stereoscopic endoscope with respect to a reference orientation (1410). In some implementations, the reference orientation can be defined as the "horizon" that is perpendicular to the direction of earth's gravity. In some implementations, the line connecting the first aperture location and the second aperture location can be substantially similar to the axis 1020 shown in FIG. 10A as passing through the locations corresponding to the LCD segments 1010*b* and 1015*b*. In some implementations, determining the reference orientation can include receiving information indicative of an orientation of the head of a user operating a stereoscopic endoscope, and determining the reference orientation in accordance with the information indicative of the orientation of the head of the user; and/or relative to a display on a wall or boom.

Operations of the process 1400 also includes adjusting at least one of the first and second aperture locations, while maintaining a spacing between the first and second aperture locations, to maintain the angle of orientation across multiple endoscope orientations (1420). This can include, for example, selecting locations of a pair of liquid crystal display (LCD) segments from a set of LCD segments disposed in a substantially annular configuration in an optical path of the stereoscopic endoscope. In some implementations, the annular configuration of the LCD segments can be substantially as shown in the example of FIG. 8B.

Operations of the process 1400 further includes creating an aperture at each of the first and second aperture locations (1430). In some implementations, this can be done, for example, using the combination of electrode arrays described above with reference to FIGS. 7A, 7B, and 8A. For example, creating the apertures can include controlling a first LCD segment in the pair of LCD segments such that the first LCD segment changes to a state in which the first LCD element allows more light to pass through as compared to a different, relatively minimally transmissive or dark state, and controlling a second LCD segment in the pair of LCD segments such that the second LCD segment changes to a state in which the second LCD segment allows more light to pass through as compared to a different, relatively minimally transmissive or dark state. In some implementations, the apertures may be created in a sequential pattern, as illustrated, for example, in FIG. 13.

Operations of the process 1400 also includes generating the 3D representation for presentation on a display device associated with the stereoscopic endoscope using signals based on light captured through the apertures created at the first and second aperture locations (1440). In some implementations, the display device can be substantially similar to a display device associated with the surgeon's console 50, as described above with reference to FIG. 2. In some cases, the process 1400 can also include receiving user input responsive to presenting the visual representation of the surgical scene on the display device. For example, the user input can pertain to operating a surgical device (such as the robotic manipulator arm assembly 120 described with reference to FIG. 3) at the surgical scene. In some implementations, the signals can correspond to a first image and a second image acquired substantially concurrently. In such concurrent acquisition, the light passing through the first LCD segment can be configured to pass through a first polarizer, and the light passing through the second LCD segment can be configured to pass through a second polarizer that polarizes light differently from the first polarizer. In some implementations, the first polarizer can be substantially orthogonal to the second polarizer.

In some implementations, the light passing through the apertures created at the first and second aperture locations is sensed using a first sensor and a second sensor, respectively. The first and second sensors can be disposed on two opposing sides of a polarizing beam splitter, such as in the arrangement described above with reference to FIG. 4. In some implementations, the light passing through the apertures created at the first and second aperture locations are sensed using a single sensor, such as in the arrangements described above with reference to FIGS. 12A and 12B.

The functionality of the tele-operated surgery system described herein, or portions thereof, and its various modifications (hereinafter "the functions") can be implemented, at least in part, via a computer program product, e.g., a computer program tangibly embodied in an information carrier, such as one or more non-transitory machine-readable media or storage device, for execution by, or to control the operation of, one or more data processing apparatus, e.g., a programmable processor, a DSP, a microcontroller, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one or more processing devices at one site, or distributed across multiple sites and interconnected by a network.

Actions associated with implementing all or part of the functions can be performed by one or more programmable processors or processing devices executing one or more computer programs to perform the functions of the processes described herein. All or part of the functions can be implemented as, special purpose logic circuitry, e.g., an FPGA and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

While this specification contains many specific implementation details, these should not be construed as limitations on what may be claimed, but rather as descriptions of features that may be specific to particular embodiments. Other embodiments may also be within the scope of the technology described herein. For example, while the technology has been described with reference to two mirrors and a single mirror bounce, the technology may be extended to any odd number of mirror bounces without deviating from the scope of this disclosure. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can, in some cases, be removed from the combination, and the claimed combination may be directed to a subcombination or variation of a subcombination.

Elements of different implementations described herein may be combined to form other embodiments not specifically set forth above. Elements may be left out of the structures described herein without adversely affecting their operation. Furthermore, various separate elements may be combined into one or more individual elements to perform the functions described herein.

What is claimed is:

1. A stereoscopic endoscope comprising:
   at least one image sensor for sensing a first image and a second image of a pair of stereo images, the first image being sensed based on light passing through a first aperture within the stereoscopic endoscope, and the second image being sensed based on light passing through a second aperture within the stereoscopic endoscope; and
   a liquid crystal layer disposed between two layers of glass comprising a first arrangement of electrodes, such that each of the first aperture and the second aperture is created in the liquid crystal layer using a portion of the first arrangement of electrodes,
   wherein a polarization state associated with each of the first and second apertures are controlled using corresponding control signals provided through the first arrangement of electrodes.

2. The stereoscopic endoscope of claim 1, wherein the liquid crystal layer is configured to rotate the light passing through the liquid crystal layer such that the light passing through the first aperture is orthogonally polarized with respect to the light passing through the second aperture.

3. The stereoscopic endoscope of claim 1, wherein the liquid crystal layer is a first liquid crystal layer and the stereoscopic endoscope further comprises a second liquid crystal layer that includes a third aperture and a fourth aperture using a portion of a second arrangement of electrodes.

4. The stereoscopic endoscope of claim 3, wherein the first image is sensed based on light passing through the first aperture and the third aperture and the second image is sensed based on light passing through the second aperture and the fourth aperture.

5. The stereoscopic endoscope of claim 1, wherein the polarization state of the first aperture and the second aperture are substantially the same.

6. The stereoscopic endoscope of claim 1, wherein a size of the first aperture and a size of the second aperture are controllable using corresponding control signals provided through the first arrangement of electrodes.

7. The stereoscopic endoscope of claim 1, wherein the liquid crystal layer is configured to polarize the light by rotating the light as it passes through the first aperture and the stereoscopic endoscope further comprises a second liquid crystal layer that is configured to further polarize the light from the first aperture.

8. The stereoscopic endoscope of claim 7, wherein the second liquid crystal layer is configured to be controlled using corresponding control signals provided through a second arrangement of electrodes.

9. The stereoscopic endoscope of claim 1, wherein the light passing through the first aperture is polarized differently as compared to the light passing through the second aperture.

10. The stereoscopic endoscope of claim 9, comprising:
    a first image sensor;
    a second image sensor; and
    an optical element that directs incident light to the first image sensor or the second image sensor based on polarization state of the incident light.

11. The stereoscopic endoscope of claim 1, wherein locations of the first and second apertures are controllable in accordance with an orientation of the stereoscopic endoscope with respect to a reference orientation.

12. The stereoscopic endoscope of claim 1, wherein a location of at least one of the first and second apertures is electronically adjusted using the first arrangement of electrodes to maintain an angle between (i) a line connecting the first and second apertures, and (ii) a reference orientation.

13. The stereoscopic endoscope of claim 12, wherein the angle between (i) the line connecting the first and second apertures, and (ii) the reference orientation is maintained.

14. The stereoscopic endoscope of claim 12, wherein the angle between (i) a line connecting the first and second apertures, and (ii) the reference orientation is maintained using one or more control signal calculated based on one or more previously captured images.

15. The stereoscopic endoscope of claim 1, wherein the liquid crystal layer comprises a plurality of regions that are selectively switchable between a first transmissive mode, and a second relatively less transmissive mode, and wherein the first aperture and the second aperture are created by energizing portions of the plurality of regions using the portion of the first arrangement of electrodes.

16. The stereoscopic endoscope of claim 1, wherein the liquid crystal layer comprises a plurality of liquid crystal segments.

17. The stereoscopic endoscope of claim 16, wherein a size of each of the first aperture and the second aperture is defined as a subset of the plurality of liquid crystal segments.

18. The stereoscopic endoscope of claim 1 wherein a polarizer associated with the first aperture is substantially orthogonal with respect to the second aperture.

19. The stereoscopic endoscope of claim 1, wherein the light passing through a first aperture is captured using a first image sensor, and the light passing through the second aperture is captured using a second image sensor, the first and second image sensors being disposed on two sides of a polarizing beam splitter.

20. The stereoscopic endoscope of claim 1, wherein the first image and second image are sensed by a single sensor sequentially.

* * * * *